United States Patent
Bertozzi et al.

(10) Patent No.: US 11,787,865 B2
(45) Date of Patent: Oct. 17, 2023

(54) BIFUNCTIONAL MOLECULES FOR LYSOSOMAL TARGETING AND RELATED COMPOSITIONS AND METHODS

(71) Applicant: The Board of Trustees of the Leland Stanford Junior University, Stanford, CA (US)

(72) Inventors: Carolyn Bertozzi, Menlo Park, CA (US); Steven Banik, Stanford, CA (US); Kayvon Pedram, Stanford, CA (US); Green Ahn, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 17/499,272

(22) Filed: Oct. 12, 2021

(65) Prior Publication Data

US 2022/0025057 A1    Jan. 27, 2022

Related U.S. Application Data

(63) Continuation of application No. 17/311,779, filed as application No. PCT/US2019/067228 on Dec. 18, 2019, now abandoned.

(60) Provisional application No. 62/932,347, filed on Nov. 7, 2019, provisional application No. 62/782,193, filed on Dec. 19, 2018.

(51) Int. Cl.
| | |
|---|---|
| *C07K 16/28* | (2006.01) |
| *A61K 47/64* | (2017.01) |
| *A61K 47/68* | (2017.01) |

(52) U.S. Cl.
CPC ...... *C07K 16/2863* (2013.01); *A61K 47/6425* (2017.08); *A61K 47/6849* (2017.08); *A61K 47/6855* (2017.08); *C07K 16/2827* (2013.01); *C07K 16/2881* (2013.01); *C07K 2317/55* (2013.01); *C07K 2317/77* (2013.01)

(58) Field of Classification Search
CPC ............ C07K 16/2863; C07K 16/2827; C07K 16/2881; C07K 2317/55; C07K 2317/77
See application file for complete search history.

(56) References Cited

U.S. PATENT DOCUMENTS

| | | | |
|---|---|---|---|
| 6,844,319 B1 | 1/2005 | Poelstra et al. |
| 7,422,902 B1 | 9/2008 | Wheeler et al. |
| 8,716,239 B2 | 5/2014 | DeFrees et al. |
| 8,962,573 B2 | 2/2015 | Garcia et al. |
| 9,545,450 B2 | 1/2017 | Do |
| 9,545,451 B2 | 1/2017 | Papadopoulos et al. |
| 9,993,546 B2 | 6/2018 | August et al. |
| 2003/0049203 A1 | 3/2003 | Elmaleh et al. |
| 2003/0152560 A1 | 8/2003 | Selden et al. |
| 2003/0211113 A1 | 11/2003 | Kakkis et al. |
| 2004/0009907 A1 | 1/2004 | Alsobrook et al. |
| 2004/0180046 A1 | 9/2004 | Himawan |
| 2006/0286087 A1 | 12/2006 | Kakkis et al. |
| 2007/0077197 A1 | 4/2007 | Wedeking et al. |
| 2007/0249682 A1 | 10/2007 | Zheng et al. |
| 2009/0238818 A1 | 9/2009 | Kakkis et al. |
| 2010/0247548 A1 | 9/2010 | Shepard et al. |
| 2011/0104076 A1 | 5/2011 | Shull |
| 2011/0104103 A1 | 5/2011 | Heetebrij et al. |
| 2012/0121592 A1 | 5/2012 | Sangkon et al. |
| 2014/0212423 A1 | 7/2014 | Hanzatian et al. |
| 2015/0094334 A1 | 4/2015 | Barnham et al. |
| 2015/0329555 A1 | 11/2015 | Liras et al. |
| 2016/0002343 A1 | 1/2016 | Hanzatian et al. |
| 2016/0060354 A1 | 3/2016 | Avila et al. |
| 2016/0082112 A1 | 3/2016 | Spiegel et al. |
| 2016/0108133 A1 | 4/2016 | Armstrong et al. |
| 2016/0136299 A1 | 5/2016 | Avila et al. |
| 2016/0166679 A1 | 6/2016 | Low et al. |
| 2016/0207953 A1 | 7/2016 | Liras et al. |
| 2016/0297861 A1 | 10/2016 | Poelstra et al. |
| 2016/0362450 A1 | 12/2016 | Schteingart et al. |
| 2017/0218378 A1 | 8/2017 | Galindo et al. |
| 2017/0232076 A1 | 8/2017 | Concino et al. |
| 2018/0265534 A1 | 9/2018 | Morere et al. |
| 2018/0355017 A1 | 12/2018 | Baik et al. |

(Continued)

FOREIGN PATENT DOCUMENTS

| | | |
|---|---|---|
| CN | 112236169 A | 1/2021 |
| EP | 2448600 | 3/2016 |

(Continued)

OTHER PUBLICATIONS

Ghosh et al., Mannose 6-phosphate receptors: new twists in the tale. Nat. Rev. Mol. Cell Biol., 4: 202-212, 2003.*
Agarwal, V. et al., "Enhancing the efficacy of cation-independent mannose 6-phosphate receptor inhibitors by intracellular delivery," Chemical Communications, vol. 52, Oct. 19, 2015, pp. 327-330.
Akinc, A. et al., "Targeted delivery of RNAi therapeutics with endogenous and exogenous ligand-based mechanisms," Molecular Therapy 18(7), Jul. 2010, pp. 1357-1364.
Andreev, J. et al., "Bispecific Antibodies and Antibody-Drug Conjugates (ADCs) Bridging HER2 and Prolactin Receptor Improve Efficacy of HER2 ADCs," Molecular Cancer Therapeutics, Jan. 20, 2017, pp. 681-693.

(Continued)

*Primary Examiner* — Ruixiang Li
(74) *Attorney, Agent, or Firm* — Brian E. Davy; Bozicevic, Field & Francis LLP

(57) ABSTRACT

Provided are bifunctional molecules that include a first moiety that specifically binds a cell surface molecule or extracellular molecule, and a second moiety that specifically binds a lysosomal targeting molecule. The bifunctional molecules find use, e.g., for targeted degradation of cell surface and extracellular molecules (e.g., proteins) via the endosomal/lysosomal pathway. Also provided are compositions and kits that include the bifunctional molecules, as well as methods of using the bifunctional molecules. Methods of making bifunctional molecules are also provided.

35 Claims, 24 Drawing Sheets

(56) References Cited

U.S. PATENT DOCUMENTS

| | | |
|---|---|---|
| 2019/0002852 A1 | 1/2019 | Vitalis et al. |
| 2019/0060481 A1 | 2/2019 | Avila et al. |
| 2019/0112588 A1 | 4/2019 | Baik et al. |
| 2019/0224282 A1 | 7/2019 | LeBowitz et al. |
| 2021/0145974 A1 | 5/2021 | Spiegel et al. |

FOREIGN PATENT DOCUMENTS

| | | |
|---|---|---|
| EP | 2009990 B1 | 9/2016 |
| EP | 3350192 | 8/2019 |
| EP | 3036257 B1 | 10/2019 |
| EP | 3773727 A1 | 2/2021 |
| WO | WO 1993/006216 A1 | 4/1993 |
| WO | WO 1995/014036 A1 | 5/1995 |
| WO | WO 1999040214 | 8/1999 |
| WO | WO 2003031464 | 4/2003 |
| WO | WO 2004/104015 A2 | 12/2004 |
| WO | WO 2005/021064 A2 | 3/2005 |
| WO | WO 2006/045505 A1 | 5/2006 |
| WO | WO 2006/052668 A2 | 5/2006 |
| WO | WO 2007/011217 A2 | 1/2007 |
| WO | 2008089339 | 7/2008 |
| WO | WO 2010/033733 A1 | 3/2010 |
| WO | WO 2010/125445 A1 | 11/2010 |
| WO | WO 2011/000958 A1 | 1/2011 |
| WO | WO 2011/038234 A2 | 3/2011 |
| WO | WO 2011/058245 A1 | 5/2011 |
| WO | WO 2013138400 | 9/2013 |
| WO | WO 2014/082080 A2 | 5/2014 |
| WO | WO 2016025519 | 2/2016 |
| WO | WO 2016/040305 A1 | 3/2016 |
| WO | WO 2017007796 | 1/2017 |
| WO | WO 2017/046535 A1 | 3/2017 |
| WO | 2017058944 | 4/2017 |
| WO | 2017134197 | 8/2017 |
| WO | WO 2017/212019 A1 | 12/2017 |
| WO | WO 2019/199621 A1 | 10/2019 |
| WO | WO 2019/199634 A1 | 10/2019 |
| WO | WO 2020/132100 A1 | 6/2020 |
| WO | WO 2021/005210 A1 | 1/2021 |
| WO | WO 2021/072246 A1 | 4/2021 |
| WO | WO 2021/072269 A1 | 4/2021 |

OTHER PUBLICATIONS

Baenziger, J.U. et al., "Galactose and N-acetylgalactosamine-specific endocytosis of glycopeptides by isolated rat hepatocytes," Cell 22(2 pt. 2), Nov. 1980, pp. 611-620.

Bocci, V., "The role of sialic acid in determining the life-span of circulating cells and glycoproteins," Experientia, vol. 32, Feb. 1976, pp. 135-140.

Braulke, T. et al., "Sorting of lysosomal proteins," Biochimica et Biophysica Acta, vol. 1793, Nov. 12, 2008, pp. 605-614.

De Goeij, B. et al., "Efficient Payload Delivery by a Bispecific Antibody-Drug Conjugate Targeting HER2 and CD63," Molecular Cancer Therapeutics 15(11), Aug. 24, 2016, pp. 2688-2697.

Devanaboyina, S.C. et al., "Engineered clearing agents for the selective depletion of antigen-specific antibodies," Nature Communications 8(15314), May 31, 2017, pp. 1-6.

Distler, J.J. et al., "The Binding Specificity of High and Low Molecular Weight Phosphomannosyl Receptors from Bovine Testes," The Journal of Biological Chemistry, vol. 266, No. 32, Nov. 15, 1991, pp. 21687-21692.

Jeanjean, A. et al., "Synthesis of new sulfonate and phosphonate derivatives for cation-independent mannose 6-phosphate receptor targeting," Bioorg Med Chem Lett 18(23), Nov. 20, 2008, pp. 6240-6243.

Kang, H.J. et al., "Cyclic peptide ligand with high binding capacity for affinity purification of immunoglobulin G", Journal of Chromatography A, vol. 1466, Sep. 30, 2016, pp. 105-112.

Kang, J-Y. et al., "Lysosomal Targeting Enhancement by Conjugation of Glycopeptides Containing Mannose-6-phosphate Glycans Derived from Glycoengineered Yeast," Scientific Reports 8(8730), Jun. 7, 2018, pp. 1-14.

Kim, J.A. et al., "Presumed LRP1-targeting transport peptide delivers β-secretase inhibitor to neurons in vitro with limited efficiency", Scientific Reports, vol. 6, 34297, Sep. 29, 2016, pp. 1-12.

Kim, K-W. et al., "Macrophage migration inhibitory factor: a potential therapeutic target for rheumatoid arthritis", The Korean Journal of Internal Medicine, vol. 31, Jul. 2016, pp. 634-642.

Kroetsch, A. et al., "Engineered pH-dependent recycling antibodies enhance elimination of Staphylococcal enterotoxin B superantigen in mice," MABS, vol. 11, No. Dec. 2018, pp. 411-421.

Krook, M. et al., "Novel peptides binding to the Fc-portion of immunoglobulins obtained from a combinatorial phage display peptide library", Journal of Immunological Methods, vol. 221, Iss. 1-2, Dec. 1998, pp. 151-157.

Landry, J.P. et al., "Discovering small molecule ligands of vascular endothelial growth factor that block VEGF-KDR binding using label-free microarray-based assays,", Assay and Drug Development Technologies 11(5), Jun. 2013, pp. 326-332.

Lee, J.H. et al., "Receptor mediated uptake of peptides that bind the human transferrin receptor", European Journal of Biochemistry, 268(7), Dec. 20, 2001, pp. 2004-2012.

Lund, L.N. et al., "Novel peptide ligand with high binding capacity for antibody purification", Journal of Chromatography A, vol. 1225, Feb. 17, 2012, pp. 158-167.

Maga, J.A. et al., "Glycosylation-independent Lysosomal Targeting of Acid α-Glucosidase Enhances Muscle Glycogen Clearance in Pompe Mice," The Journal of Biological Chemistry, vol. 288, No. 3, Jan. 18, 2013, pp. 1428-1438.

Mamidyala, S.K. et al., "Glycomimetic Ligands for the Human Asialoglycoprotein Receptor," Journal of the American Chemical Society, vol. 134, Jan. 24, 2012, pp. 1978-1981.

Matsuda, S. et al., "siRNA conjugates carrying sequentially assembled trivalent N-acetylgalactosamine linked through nucleosides elicit robust gene silencing in vivo in hepatocytes," ACS Chem Biol., vol. 10, Mar. 2, 2015, pp. 1181-1187.

Mcenaney, P.J. et al., "Antibody-Recruiting Molecules: An Emerging Paradigm for Engaging Immune Function in Treating Human Disease", ACS Chem. Biol. (7), Jul. 3, 2012, pp. 1139-1151.

Menegatti, S. et al., "Design of protease-resistant peptide ligands for the purification of antibodies from human plasma", Journal of Chromatography A, vol. 1445, May 6, 2016, pp. 93-104.

Menegatti, S. et al., "mRNA display selection and solid-phase synthesis of Fc-binding cyclic peptide affinity ligands", Biotechnology and Bioengineering 110(3), Mar. 2013, pp. 857-870.

Menegatti, S. et al., "Reversible cyclic peptide libraries for the discovery of affinity ligands", Anal. Chem., vol. 85, No. 19, Sep. 3, 2013, pp. 9229-9237.

Merwin, J. R. et al., "Targeted Delivery of DNA Using YEE(GalNAcAH)3, a Synthetic Glycopeptide Ligand for the Asialoglycoprotein Receptor," Bioconjugate Chem. 5(6), Nov. 1, 1994, pp. 612-620.

Mezo, A.R. et al., "Reduction of IgG in nonhuman primates by a peptide antagonist of the neonatal Fc receptor FcRn", Proceedings of the National Academy of Sciences 105(7), Feb. 19, 2008, pp. 2337-2342.

Molino, Y. et al., "Use of LDL receptor-targeting peptide vectors for in vitro and in vivo cargo transport across the blood-brain barrier", The FASEB Journal, 31(5), Jan. 20, 2017, pp. 1807-1827.

Mu, L-M. et al., "Lipid vesicles containing transferrin receptor binding peptide TfR-T12 and octa-arginine conjugate stearyl-R8 efficiently treat brain glioma along with glioma stem cells", Scientific Reports, 7(1), Jun. 14, 2017, pp. 1-12.

Nair, J.K. et al., "Multivalent N-Acetylgalactosamine-Conjugated siRNA Localizes in Hepatocytes and Elicits Robust RNAi-Mediated Gene Silencing," Journal of the American Chemical Society, vol. 136, Dec. 1, 2014, pp. 16958-16961.

Nalawansha, D.A., et al., "Targeted Protein Internalization and Degradation by ENDosome Targeting Chimeras", ACS Central Science 5(6), May 9, 2019, pp. 1079-1084.

(56) References Cited

OTHER PUBLICATIONS

Neven, C. et al., "Macrophage Scavenger Receptor A Mediates Adhesion to Apolipoproteins A-I and E", Biochemistry 48(50), Nov. 13, 2009, 11858-11871.
Palaniappan, K.K. et al., "Chemical Glycoproteomics," Chemical Reviews, vol. 116, Nov. 18, 2016, pp. 14277-14306.
Parker, C.G. et al., "Illuminating HIV gp 120-ligand recognition through computationally-driven optimization of antibody-recruiting molecules", Chemical Science, Iss. 6, Apr. 2, 2014, pp. 2311-2317.
Prakash, J. et al., "Tumor-targeted intracellular delivery of anticancer drugs through the mannose-6-phosphate/insulin-like growth factor II receptor," International Journal of Cancer, vol. 126, Sep. 30, 2009, pp. 1966-1981.
Pujol, A.M. et al., "Hepatocyte Targeting and Intracellular Copper Chelation by a Thiol-Containing Glycocyclopeptide," J. Am. Chem. Sec., vol. 133, No. 2, Dec. 14, 2010, pp. 286-296.
Reddy Bonam, S. et al., "Lysosomes as a therapeutic target," Nature Reviews, vol. 18, Dec. 2019, pp. 923-948.
Reidy, T. et al., "Homotrimeric macrophage migration inhibitory factor (MIF) drives inflammatory responses in the corneal epithelium by promoting caveolin-rich platform assembly in response to infection", Journal of Biological Chemistry, vol. 288, Iss. 12, Mar. 2013, pp. 8269-8278.
Rensen, P.C.N. et al., "Design and Synthesis of Novel N-Acetylgalactosamine-Terminated Glycolipids for Targeting of Lipoproteins to the Hepatic Asialoglycoprotein Receptor," Journal of Medicinal Chemistry, vol. 47, No. 23, Oct. 6, 2004, pp. 5798-5808.
Rensen, P.C.N. et al., "Determination of the Upper Size Limit for Uptake and Processing of Ligands by the Asialoglycoprotein Receptor on Hepatocytesin Vitro and in Vivo," Glycobiology and Extracellular Matrices, vol. 276, Iss. 40, Oct. 2001, pp. P37577-37584.
Ribeiro, S.M.F. et al., "The Activation Sequence of Thrombospondin-1 Inter-acts with the Latency-associated Peptide to Regulate Activation of Latent Transforming Growth Factor", The Journal of Biological Chemistry, vol. 274, Iss. 19, May 1999, pp. 13586-13593.
Ruan, H. et al., "A novel peptide ligand RAP12 of LRP1 for glioma targeted drug delivery," Journal of Controlled Release, vol. 279, Jun. 10, 2018, pp. 306-315.
Rullo, A.F. et al., "Re-engineering the Immune Response to Metastatic Cancer: Antibody-Recruiting Small Molecules Targeting the Urokinase Receptor", Angew. Chem. Int. Ed, Feb. 15, 2016, pp. 3642-3646.
Saftig, P. et al., "Lysosome biogenesis and lysosomal membrane proteins: trafficking meets function," Nature Reviews, vol. 10, Sep. 2009, pp. 623-635.
Sakamoto, K. et al., "A novel LRP1-binding peptide L57 that crosses the blood brain barrier", Biochemistry and Biophysics Reports, vol. 12, Dec. 2017, pp. 135-139.
Sanhueza, C.A. et al., "Efficient Liver Targeting by Polyvalent Display of a Compact Ligand for the Asialoglycoprotein Receptor", Journal of the American Chemical Society, vol. 139, Feb. 23, 2017, pp. 3528-3536.
Santi , M. et al., "Rational design of a transferrin-binding peptide sequence tailored to targeted nanoparticle internalization", Bioconjugate Chemistry, 28(2), Dec. 1, 2016, pp. 471-480.
Schwartz, A.L. et al., "Characterization of the asialoglycoprotein receptor in a continuous hepatoma line", Journal of Biological Chemistry, vol. 256, Iss. 17, Sep. 10, 1981, pp. 8878-8881.
Segers, F.M.E. et al., "Scavenger Receptor-AI-Targeted Iron Oxide Nanoparticles for In Vivo MRI Detection of Atherosclerotic Lesions", Arteriosclerosis, Thrombosis, and Vascular Biology, 32(4), Jan. 26, 2012, pp. 971-978.
Sugita, T. et al., "Screening of peptide ligands that bind to the Fe region of IgG using peptide array and its application to affinity purification of antibody", Biochemical Engineering Journal, vol. 79, Oct. 15, 2013, pp. 33-40.
Tian, W. et al., "The glycosylation design space for recombinant lysosomal replacement enzymes produced in CHO cells," Nature Communications 10(1785), Apr. 30, 2019, pp. 1-13.
Toldo, S. et al., "Low-Density Lipoprotein Receptor-Related Protein-1 Is a Therapeutic Target in Acute Myocardial Infarction", JACC: Basic to Translational Science 2(5), Oct. 2017, pp. 561-574.
Tong, P.Y. et al., "Ligand Interactions of the Cation-dependent Mannose 6-Phosphate Receptor," The Journal of Biological Chemistry, vol. 264, No. 14, May 15, 1989, pp. 7970-7975.
Tsai , C-W. et al., "Strategy of Fe-recognizable peptide ligand design for oriented immobilization of antibody", Anal. Chem., vol. 86, No. 6, Feb. 17, 2014, pp. 2931-2938.
Verdoliva, A. "A new ligand for immunoglobulin G subdomains by screening of a synthetic peptide library", ChemBioChem 6(7), Jul. 2005, pp. 1242-1253.
Verdoliva, A. et al., "Affinity purification of polyclonal antibodies using a new all-D synthetic peptide ligand comparison with protein A and protein G", Journal of Immunological Methods, vol. 271, Iss. 1-2, Dec. 20, 2002, pp. 77-88.
Wang, Y. et al., "Pharmacokinetics and Clinical Pharmacology Considerations of GalNAc3-Conjugated Antisense Oligonucleotides," Expert Opinion on Drug Metabolism & Toxicology, vol. 15, No. 6, May 30, 2019, pp. 475-485.
Wangler, C. et al., "In Vitro and Initial In Vivo Evaluation of 68Ga-Labeled Transferrin Receptor (TfR) Binding Peptides as Potential Carriers for Enhanced Drug Transport into TfR Expressing Cells", Molecular Imaging and Biology, 13(2), May 15, 2010, pp. 332-341.
Watarai, H. et al., "Posttranslational modification of the glycosylation inhibiting factor (GIF) gene product generates bioactive GIF", Proceedings of the National Academy of Sciences 97(24), Nov. 21, 2000, pp. 13251-13256.
Willis, M.S. et al., "Macrophage migration inhibitory factor mediates late cardiac dysfunction after burn injury", American Journal of Physiology-Heart and Circulatory Physiology, vol. 288, Feb. 1, 2005, pp. H795-H804.
Yang, H. et al., "Hexamer peptide affinity resins that bind the Fe region of human immunoglobulin G", The Journal of Peptide Research, vol. 66, Iss. 1, Dec. 2005, pp. 120-137.
Yang, H. et al., "Purification of human immunoglobulin G via Fe-specific small peptide Tigand affinity chromatography", Journal of Chromatography A, vol. 1216, Iss. 6, Feb. 6, 2009, pp. 910-918.
Yoo, R-J. et al., "Identification of a peptide ligand for antibody immobilization on biosensor surfaces", BioChip Journal, vol. 10, Dec. 18, 2015, pp. 88-94.
Zavorka, M.E. et al., "Inhibition of insulin-like growth factor II (IGF-II)-dependent cell growth by multidentate pentamannosyl 6-phosphate-based ligands targeting the mannose 6-phosphate/IGF-II receptor," Oncotarget, vol. 7, No. 38, Aug. 22, 2016, pp. 62386-62410.
Zhang, Y. et al., "Identification of a Small Peptide That Inhibits PCSK9 Protein Binding to the Low Density Lipoprotein Receptor", The Journal of Biological Chemistry, vol. 289, Iss. 2, Jan. 2014, pp. 942-955.
Zhao, W-W. et al., "Biomimetic design of affinity peptide ligands for human IgG based on protein A-IgG complex", Biochemical Engineering Journal, vol. 88, Jul. 15, 2014, pp. 1-11.
Zhao, W-W. et al., "Dual-ligand affinity systems with octapeptide ligands for affinity chromatography of hIgG and monoclonal antibody", Journal of Chromatography A, vol. 1359, Nov. 21, 2014, pp. 64-72.
Zhao, W-W. et al., "FYWHCLDE-based affinity chromatography of IgG: effect of Tigand density and purifications of human IgG and monoclonal antibody", Journal of Chromatography A, vol. 1355, Aug. 15, 2014, pp. 107-114.
Zhao, W-W. et al., "Octapeptide-based affinity chromatography of human immunoglobulin G: comparisons of three different ligands", Journal of Chromatography A, vol. 1359, Sep. 12, 2014, pp. 100-111.
Zhu, Y. et al., "Conjugation of mannose 6-phosphate-containing oligosaccharides to acid alpha-glucosidase improves the clearance of glycogen in pompe mice," The Journal of Biological Chemistry 279(48), Nov. 26, 2004, pp. 50336-50341.
D'Souza and Devarajan (2015) "Asialoglycoprotein receptor mediated hepatocyte targeting—Strategies and applications" Journal of Controlled Release, 203:126-139.

(56) References Cited

OTHER PUBLICATIONS

Gary-Bobo et al. (2007) "Mannose 6-phosphate receptor targeting and its applications in human diseases" Curr Med Chem., 14(28):2945-2953.
Ganesa et al. (2011) "Rapid and Efficient Clearance of Blood-borne Virus by Liver Sinusoidal Endothelium" PLoS, 7(9):e1002281.
Huang et al. (2017) "Well-Defined Multivalent Ligands for Hepatocytes Targeting via Asialoglycoprotein Receptor" Bioconjug Chem., 28(2):283-295.
Third Party Observation for International Appln. No. PCT/US2019/067228, 4 pages.
Banik, S. et al., "Lysosome Targeting Chimeras (LYTACs) for the Degradation of Secreted and Membrane Proteins" Nov. 20, 2019, pp. 1-64. doi.org/10.26434/chemrxiv.7927061.v2.
Banik, S.M. et al., "Lysosome Targeting Chimeras (LYTACs) for the Degradation of Secreted and Membrane Proteins" Mar. 29, 2019, pp. 1-68. doi.org/10.26434/chemrxiv.7927061.v1.
Barragan, V. et al., "A mannose-6-phosphonate—cholesterylamine conjugate as a specific molecular adhesive linking cancer cells with vesicles," Chemical Communications, Dec. 14, 2000, pp. 85-86.
Beljaars, L. et al., "Albumin Modified With Mannose 6-Phosphate: A Potential Carrier for Selective Delivery of Antifibrotic Drugs to Rat and Human Hepatic Stellate Cells," HEPATOLOGY vol. 29, No. 5, May 1999, pp. 1486-1493.
Das, S. et al., "Controlled Synthesis of End-Functionalized Mannose-6-phosphate Glycopolypeptides for Lysosome Targeting," ACS Macro Letters, vol. 5, Jun. 22, 2016, pp. 809-813.
Liu, C., "Design, Synthesis and Evaluation of Bivalent Inhibitors of Trehalose-6-Phosphate Phosphatase," University of New Mexico, Electronic Theses and Dissertations, Jun. 2015, pp. 1-250.
PCT International Search Report and Written Opinion, PCT Application No. PCT/US2019/026239, dated Aug. 8, 2019.
PCT International Search Report and Written Opinion, PCT Application No. PCT/US2019/026260, dated Aug. 15, 2019, 14 pages.
Roseng, L. et al., "Uptake, intracellular transport, and degradation of polyethylene glycol-modified asialofetuin in hepatocytes," The Journal of Biological Chemistry 267(32), Nov. 1992, pp. 22987-22993.
Stokmaier, D., "Targeting Hepatocytes via the Asialoglycoprotein-Receptor," Inaugural Dissertation, Basel, Dec. 14, 2010, pp. 3-149.
Yang, N. et al., "HPMA Polymer-based Site-specific Delivery of Oligonucleotides to Hepatic Stellate Cells" Bioconjug Chem. 20(2), Jan. 9, 2009, pp. 213-221.
Ye, Z. et al., "Targeted delivery of a triplex-forming oligonucleotide to hepatic stellate cells," Biochemistry 44(11), Mar. 22, 2005, pp. 4466-4476.
Zhang, H et al., "Recent developments in carbohydrate-decorated targeted drug/gene delivery", Medicinal research reviews 30.2 (2010): 270-289.
Borden et al. (1990) "Acidification-dependent Dissociation of Endocytosed Insulin Precedes That of Endocytosed Proteins Bearing the Mannose 6-Phosphate Recognition Marker" The Journal of Bio. Chem. 1265(15):8497-8504.
Maxfield and McGraw (2004) "Endocytic Recycling" Nature Reviews, 5:121-132.
Sahagian and Neufeld (1983) "Biosynthesis and Turnover of the Mannose 6-Phosphate Receptor in Cultured Chinese Hamster Ovary Cells" The Journal of Bio. Chem. 258(11):7121-7128.
Banik et al. (2020) "Lysosome-targeting chimaeras for degradation of extracular proteins" Nature, 584(7820):291-297.

\* cited by examiner

BIFUNCTIONAL MOLECULES FOR LYSOSOMAL TARGETING AND RELATED COMPOSITIONS AND METHODS

CROSS-REFERENCE TO RELATED APPLICATIONS

The present application is a continuation application of U.S. patent application Ser. No. 17/311,779, filed on Jun. 8, 2021, which is a 371 National Phase patent application of PCT Application Serial No. PCT/US2019/067228, filed on Dec. 18, 2019, which claims the benefit of U.S. Provisional Patent Application No. 62/782,193, filed Dec. 19, 2018, and U.S. Provisional Patent Application No. 62/932,347, filed Nov. 7, 2019, which applications are incorporated herein by reference in their entireties.

STATEMENT OF GOVERNMENT SUPPORT

This invention was made with Government support under contracts CA227942, GM059907, and GM123636 awarded by the National Institutes of Health. The Government has certain rights in the invention.

SUMMARY

Provided are bifunctional molecules that include a first moiety that specifically binds a cell surface molecule or extracellular molecule, and a second moiety that specifically binds a lysosomal targeting molecule. The bifunctional molecules find use, e.g., for targeted degradation of cell surface and extracellular molecules (e.g., proteins) via the endosomal/lysosomal pathway. Also provided are compositions and kits that include the bifunctional molecules, as well as methods of using the bifunctional molecules. Methods of making bifunctional molecules are also provided.

DETAILED DESCRIPTION

Figure 1:
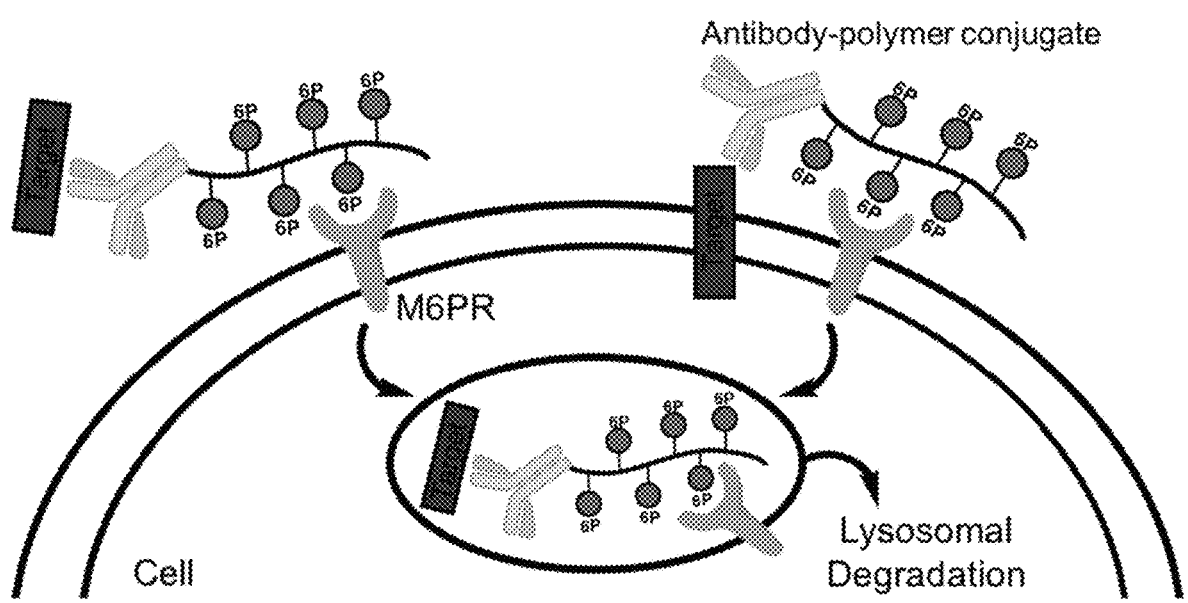
FIG. 1 A schematic illustration of a bifunctional molecule and use thereof according to one embodiment of the present disclosure.

Provided are bifunctional molecules that include a first moiety that specifically binds a cell surface molecule or extracellular molecule, and a second moiety that specifically binds a lysosomal targeting molecule. The bifunctional molecules find use, e.g., for targeted degradation of cell surface and extracellular molecules (e.g., proteins) via the endosomal/lysosomal pathway. Also provided are compositions and kits that include the bifunctional molecules, as well as methods of using the bifunctional molecules. Methods of making bifunctional molecules are also provided.

Before the bifunctional molecules, compositions, kits and methods of the present disclosure are described in greater detail, it is to be understood that the bifunctional molecules, compositions, kits and methods are not limited to particular embodiments described, as such may, of course, vary. It is also to be understood that the terminology used herein is for the purpose of describing particular embodiments only, and is not intended to be limiting, since the scope of the bifunctional molecules, compositions, kits and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the bifunctional molecules, compositions, kits and methods. The upper and lower limits of these smaller ranges may independently be included in the smaller ranges and are also encompassed within the bifunctional molecules, compositions, kits and methods, subject to any specifically excluded limit in the stated range. Where the stated range includes one or both of the limits, ranges excluding either or both of those included limits are also included in the bifunctional molecules, compositions, kits and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the bifunctional molecules, compositions, kits and methods belong. Although any bifunctional molecules, compositions, kits and methods similar or equivalent to those described herein can also be used in the practice or testing of the bifunctional molecules, compositions, kits and methods, representative illustrative bifunctional molecules, compositions, kits and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present bifunctional molecules, compositions, kits and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the bifunctional molecules, compositions, kits and methods, which are, for clarity, described in the context of separate embodiments, may also be provided in combination in a single embodiment. Conversely, various features of the bifunctional molecules, compositions, kits and methods, which are, for brevity, described in the context of a single embodiment, may also be provided separately or in any suitable sub-combination. At combinations of the embodiments are specifically embraced by the present disclosure and are disclosed herein just as if each and every combination was individually and explicitly disclosed, to the extent that such combinations embrace operable processes and/or compositions. In addition, at sub-combinations listed in the embodiments describing such variables are also specifically embraced by the present bifunctional molecules, compositions, kits and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Bifunctional Molecules

The present disclosure provides bifunctional molecules that include a first moiety that specifically binds a cell surface molecule or extracellular molecule, and a second moiety that specifically binds a lysosomal targeting molecule. Certain non-limiting embodiments of the bifunctional molecules will now be described.

As summarized above, the bifunctional molecules of the present disclosure include a first moiety that specifically binds a cell surface molecule or extracellular molecule. In some embodiments, the first moiety specifically binds a cell surface molecule. By "cell surface molecule" is meant a molecule associated with a cell membrane, e.g., because the molecule has a domain that inserts into or spans a cell membrane, e.g., a cell membrane-tethering domain or a transmembrane domain. The cell surface molecule may be any cell surface molecule which is desired for targeted degradation via the endosomal/lysosomal pathway. In some embodiments, the cell surface molecule is a cell surface receptor. Cell surface receptors of interest include, but are not limited to, stem cell receptors, immune cell receptors, growth factor receptors, cytokine receptors, hormone receptors, receptor tyrosine kinases, a receptor in the epidermal growth factor receptor (EGFR) family (e.g., HER2 (human epidermal growth factor receptor 2), etc.), a receptor in the fibroblast growth factor receptor (FGFR) family, a receptor in the vascular endothelial growth factor receptor (VEGFR) family, a receptor in the platelet derived growth factor receptor (PDGFR) family, a receptor in the rearranged during transfection (RET) receptor family, a receptor in the Eph receptor family, a receptor in the discoidin domain receptor (DDR) family, and a mucin protein (e.g., MUC1). In some embodiments, the cell surface molecule is CD71 (transferrin receptor). In certain aspects, the cell surface receptor is an immune cell receptor selected from a T cell receptor, a B cell receptor, a natural killer (NK) cell receptor, a macrophage receptor, a monocyte receptor, a neutrophil receptor, a dendritic cell receptor, a mast cell receptor, a basophil receptor, and an eosinophil receptor.

In some embodiments, the first moiety specifically binds a cell surface molecule which mediates its effect not through a specific molecular interaction (and therefore is not susceptible to blocking), but rather through bulk biophysical or aggregate effects. A non-limiting example of such a cell surface molecule is a mucin. Examples of mucins include, but are not limited to, MUC1, MUC16, MUC2, MUC5AC, MUC4, CD43, CD45, GPIb, and the like.

In some embodiments, when the first moiety specifically binds a cell surface molecule, the cell surface molecule is present on a cancer cell. By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised nonhuman animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a hematological malignancy (e.g., a leukemia cell, a lymphoma cell, a myeloma cell, etc.), a primary tumor, a metastatic tumor, and the like. In some embodiments, the cell surface molecule present on the cancer cell is a tumor-associated antigen or a tumor-specific antigen.

In certain aspects, when the first moiety specifically binds a cell surface molecule, the cell surface molecule is present on an immune cell. In some embodiments, the cell surface molecule is present on an immune cell selected from a T cell, a B cell, a natural killer (NK) cell, a macrophage, a monocyte, a neutrophil, a dendritic cell, a mast cell, a basophil, and an eosinophil. In certain aspects, the cell surface molecule present on the immune cell is an inhibitory immune receptor. As used herein, an "inhibitory immune receptor" is a receptor present on an immune cell that negatively regulates an immune response. Examples of inhibitory immune receptors which may be inhibited according to the methods of the present disclosure include inhibitory immune receptors of the Ig superfamily, including but not limited to: CD200R, CD300a (IRp60; mouse MAIR-I), CD300f (IREM-1), CEACAM1 (CD66a), FcγRIIb, ILT-2 (LIR-1; LILRB1; CD85j), ILT-3 (LIR-5; CD85k; LILRB4), ILT-4 (LIR-2; LILRB2), ILT-5 (LIR-3; LILRB3; mouse PIR-B); LAIR-1, PECAM-1 (CD31), PILR-α (FDF03), SIRL-1, and SRP-α. Further examples of inhibitory immune receptors which may be inhibited according to the methods of the present disclosure include sialic acid-binding Ig-like lectin (Siglec) receptors, e.g., Siglec 7, Siglec 9, and/or the like. Additional examples of inhibitory immune receptors which may be inhibited according to the methods of the present disclosure include C-type lectins, including but not limited to: CLEC4A (DCIR), Ly49Q and MICL. Details regarding inhibitory immune receptors may be found, e.g., in Steevels et al. (2011) Eur. J. Immunol. 41(3):575-587. In some embodiments, the cell surface molecule present on the immune cell is a ligand of an inhibitory immune receptor. In certain aspects, the cell surface molecule present on the immune cell is an immune checkpoint molecule. Non-limiting examples of immune checkpoint molecules to which the first moiety may specifically bind include PD-1, PD-L1, CTLA4, TIM3, LAG3, TIGIT, and a member of the B7 family.

As summarized above, the bifunctional molecules of the present disclosure include a first moiety that specifically binds a cell surface molecule or extracellular molecule. In some embodiments, the first moiety specifically binds an extracellular molecule. By "extracellular molecule" is meant a soluble molecule external to the cell membranes of any cells in the vicinity of the soluble molecule. The extracellular molecule may be any extracellular molecule which is desired for targeted degradation via the endosomal/lysosomal pathway. In some embodiments, the extracellular molecule is a ligand for a cell surface receptor. Cell surface receptor ligands of interest include, but are not limited to, growth factors (e.g., epidermal growth factor (EGF), vascular endothelial growth factor (VEGF), and the like), cytokines (e.g., an interleukin, an interferon, a tumor necrosis factor (TNF), a transforming growth factor β (TGF-β), including any particular subtypes of such cylokines), hormones, and the like. In certain aspects, the first moiety specifically binds apolipoprotein E4 (ApoE4).

In some embodiments, the first moiety specifically binds an extracellular molecule, where the extracellular molecule is an antibody, e.g., an antibody that specifically binds a cell surface molecule or different extracellular molecule. In some embodiments, the antibody is an autoantibody. Non-limiting examples of autoantibodies include rheumatoid factor (RF), antinuclear antibody (ANA), Antineutrophil Cytoplasmic Antibodies (ANCA), Anti-Double Stranded DNA (anti-dsDNA), Anticentromere Antibodies (ACA), Antihistone Antibodies, Cyclic Citrullinated Peptide Antibodies (CCP), Extractable Nuclear Antigen Antibodies (e.g., anti-SS-A (Ro) and anti-SS-B (La), anti-RNP, anti-Jo-1, anti-Sm, Scl-70), Cardiolipin Antibodies, Beta-2 Glycoprotein 1 Antibodies, Antiphospholipid Antibodies (APA). Lupus anticoagulants (LA), Diabetes-related Autoantibodies, Anti-Tissue Transglutaminase (anti-tTC), Anti-Gliadin Antibodies (AGA), Intrinsic Factor Antibodies, Parietal Cell Antibodies, Thyroid Autoantibodies (e.g., anti-TPO, TSH receptor antibodies), Smooth Muscle Antibodies (SMA), Antimitochondrial Antibodies (AMA), Liver Kidney Microsome Type 1 Antibodies (anti-LKM-1), Anti-Glomerular Basement Membrane (GBM), Acetylcholine Receptor (AChR) Antibodies, etc.

In some embodiments, the first moiety specifically binds an extracellular molecule, where the extracellular molecule is a secreted protein that accumulates in disease (e.g., alpha-synuclein), a cholesterol carrier (e.g., ApoB), an infectious disease toxin (e.g., AB toxins, ESAT-6), an infectious particle (e.g., a whole virus, a whole bacterium, etc.), a clotting factor (e.g., Factor IX), the target of any FDA approved antibody that binds to an extracellular molecule (e.g., TNFalpha), any chemokine or cytokine (e.g., mediators of sepsis or chronic inflammation such at IL-1), a proteinaceous hormone (e.g., insulin, ACTH, etc.), a proteinaceous mediator of a mood disorder, a proteinaceous mediator of energy homeostasis (e.g., leptin, ghrelin, etc.), a proteinaceous allergen present in the bloodstream or an antibody against such an allergen (e.g., for peanut allergies), a proteinaceous toxin (e.g., snake venom hyaluronidase, etc.), etc.

In certain embodiments, the first moiety specifically binds a cell surface or extracellular molecule, where the cell surface or extracellular molecule is a mutated protein. In some embodiments, the bifunctional molecule causes shuttling of the mutated protein into the lysosome, promoting its loading onto a major histocompatibility complex (MHC) (e.g., MHC I or MHC II), and thereby promoting recognition of the mutated protein by the immune system. In this context, the bifunctional molecule finds use in generating antibodies specific to a mutated and unwanted protein (e.g., KIT).

By "specifically binds" is meant the first moiety and the second moiety bind to their respective targets with an affinity or $K_a$ (that is, an equilibrium association constant of a particular binding interaction with units of 1/M) of, for example, greater than or equal to about $10^5$ $M^{-1}$. In certain embodiments, the first moiety and the second moiety bind to their respective targets with a $K_a$ greater than or equal to about $10^8$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding refers to binding with a $K_a$ of at least $10^7$ $M^{-1}$, at least $10^{13}$ $M^{-1}$, at least $10^9$ $M^{-1}$, at least $10^{10}$ $M^{-1}$, at least $10^{11}$ $M^{-1}$, at least $10^{12}$ M$^{-1}$, at least $10^{13}$ M$^{-1}$, or greater. Alternatively, affinity may be defined as an equilibrium dissociation constant ($K_D$) of a particular binding interaction with units of M (e.g., $10^{-5}$ M to $10^{-13}$ M, or less). In certain aspects, specific binding means the first moiety and the second moiety bind to their respective targets with a $K_D$ of less than or equal to about $10^{-5}$ M, less than or equal to about $10^{-6}$ M, less than or equal to about $10^{-7}$ M, less than or equal to about $10^{-8}$ M, or less than or equal to about $10^{-9}$ M, $10^{-10}$ M, $10^{-11}$ M, or $10^{-12}$ M or less. The binding affinity of the first moiety and the second moiety to their respective targets can be readily determined using conventional techniques, e.g., by competitive ELISA (enzyme-linked immunosorbent assay), equilibrium dialysis, by using surface plasmon resonance (SPR) technology (e.g., the BIAcore 2000 instrument, using general procedures outlined by the manufacturer); by radioimmunoassay; or the like.

The first moiety may be any type moiety capable of binding to the cell surface molecule or extracellular molecule to be targeted for degradation via the endosoma/lysosomal pathway. In certain aspects, the first moiety is selected from a polypeptide, a ligand (e.g., a ligand for a cell surface receptor, where the cell surface receptor is targeted for degradation), an aptamer, a nanoparticle, and a small molecule. The second moiety may be any type moiety capable of binding to the lysosomal targeting molecule. In certain aspects, the second moiety is selected from a polypeptide, a ligand (e.g., a ligand for the lysosomal targeting molecule), an aptamer, a nanoparticle, and a small molecule.

In some embodiments, when a moiety of the bifunctional molecule is a polypeptide, the moiety is an antibody. The terms "antibody" and "immunoglobulin" include antibodies or immunoglobulins of any isotype (e.g., IgG (e.g., IgG1, IgG2, IgG3 or IgG4), IgE, IgD, IgA, IgM, etc.), whole antibodies (e.g., antibodies composed of a tetramer which in turn is composed of two dimers of a heavy and light chain polypeptide); single chain antibodies; fragments of antibodies (e.g., fragments of whole or single chain antibodies) which retain specific binding to the cell surface molecule or extracellular molecule (in the case of the first moiety) or lysosomal targeting molecule (in the case of the second moiety), including, but not limited to, Fv, single chain Fv (scFv), Fab, F(ab')$_2$, Fab', (scFv')$_2$, diabodies, and nanobodies; chimeric, antibodies; monoclonal antibodies; fully human antibodies; humanized antibodies (e.g., humanized whole antibodies, humanized antibody fragments, etc.); and fusion proteins including an antigen-binding portion of an antibody and a non-antibody protein or fragment thereof. The antibodies may be detectably labeled, e.g., with an in vivo imaging agent, or the like. The antibodies may be further conjugated to other moieties, such as, e.g., polyethylene glycol (PEG), etc. Fusion to an antibody Fc region (or a fragment thereof), conjugation to PEG, etc. may find use, e.g., for increasing serum half-life of the antibody upon administration to the subject.

By "small molecule" is meant a compound having a molecular weight of 1000 atomic mass units (amu) or less. In some embodiments, the small molecule is 750 amu or less, 500 amu or less, 400 amu or less, 300 amu or less, or 200 amu or less. In certain aspects, the small molecule is not made of repeating molecular units such as are present in a polymer.

As summarized above, the second moiety specifically binds a lysosomal targeting molecule. As used herein, a "lysosomal targeting molecule" is a cell surface molecule which, upon being bound by the second moiety of the bifunctional molecule, shuttles the bifunctional molecule and cell surface molecule or extracellular molecule bound by the first moiety to the lysosome within the cell. Upon delivery and internalization into the lysosome, the bifunctional molecule and cell surface molecule or extracellular molecule are degraded by lysosomal enzymes, e.g., acid hydrolases. In this way, the bifunctional molecule targets the cell surface molecule or extracellular molecule bound by the first moiety for degradation, which targeting finds use in a variety of in vitro and in vivo applications, including research and clinical applications.

The second moiety may bind to any suitable lysosomal targeting molecule. Non-limiting examples of lysosomal targeting molecules include a mannose-6-phosphate receptor (M6PR), sortilin, folate receptor, ASPGR, IFITM3, molecules in the endosome/lysosome pathway (e.g., LIMP-1, LIMP-2), etc.

In some embodiments, the lysosomal targeting molecule to which the second moiety binds is a mannose-6-phosphate receptor (M6PR). M6PRs are present throughout the tissues of the body and are responsible for trafficking mannose-6-phosphate (M6P)-tagged cargo, such as acid hydrolases, from the Golgi compartment and extracellular space to the lysosome. Details regarding M6PRs may be found, e.g., in Gary-Bobo et al. (2007) Curr. Med. Chem. 14:2945-2953; Das et al. (2016) ACS Macro Lett. 5:809-813; and elsewhere. Examples of M6PRs to which the second moiety may bind include the cation-dependent human M6PR provided as UniProtKB-P20645 and the cation-independent M6PR provided as UniProtKB-P11717 (also referred to as insulin-like growth factor 2 receptor (IGF2R)). The cation-independent mannose 6-phosphate receptor is a multifunctional protein which binds at the cell surface to ligands such as mannose 6-phosphate (M6P) bearing proteins, IGF-II, retinoic acid, plasminogen, etc. Its major function is to bind and transport M6P-enzymes to lysosomes, but it can also modulate the activity of a variety of extracellular M6P-glycoproteins, e.g., latent TGFβ precursor, urokinase-type plasminogen activator receptor, granzyme B, growth factors, herpes virus, etc.

In certain aspects, when the lysosomal targeting molecule is an M6PR, the second moiety is an antibody that specifically binds the M6PR. Anti-M6PR antibodies are available and include the MOB-1772z recombinant anti-human M6PR antibody (Creative Biolabs), the EPR6599, 2G11, MEM-238, EPR6599, and EPR7691 anti-M6PR antibodies (Abcam), and the like.

In some embodiments, when the lysosomal targeting molecule is an M6PR, the second moiety includes one or more M6PR ligands. In certain aspects, the one or more M6PR ligands include one or more mannose-6-phosphates (M6Ps), where M6P has the following structure:

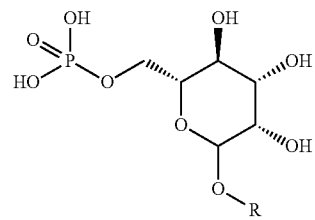

Alternatively, or additionally, the one or more M6PR ligands include one or more M6P analogs. By "M6P analog" is meant a molecule that is not M6P but binds to an M6P recognition site of M6PR. Several M6P analogs with phosphonate, carboxylate, sulfate, sulfonate or malonate groups display a higher affinity and a stronger stability in human serum than M6P itself. Some structural features have been shown to be important for the binding of M6P to M6PR. For example, the hydroxyl group at the 2-position of the pyranose ring is axial, strong binding to M6PR is observed. The distance between the negative charge and the pyranose ring also plays a role in M6P recognition by M6PR. It has been shown that suitable analogs: should generally be isosteric M6P to efficiently bind M6PR; a single negative charge is sufficient to allow binding to M6PR while the phosphorus atom is not necessary to ensure recognition; and the presence of two negative charges (as in the maionate and phosphonate isosteric analogs of M6P) is beneficial for binding to M6PR. In some embodiments, when the one or more M6PR ligands include one or more M6PR analogs, the one or more M16PR analogs include one or more phosphonate M6P analogs (M6Pn), malonate M6P analogs, carboxylate M6P analogs, sulfonate M6P analogs, acrylate M6P analogs, and/or the like. In some embodiments, the one or more M6PR analogs include one or more phosphonate M6P analogs (M6Pn) having the structure (where $M^+$ is any countercation or hydrogen atom):

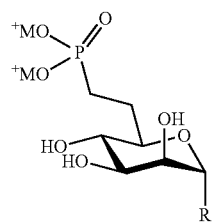

In some embodiments, the one or more M6PR analogs include one or more carboxylate M6P analogs having one of the following structures (where $M^+$ is any countercation or hydrogen atom):

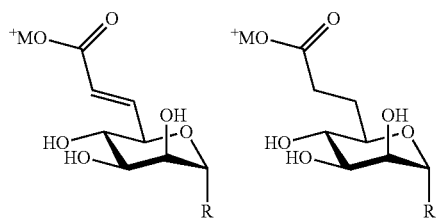

In some embodiments, the one or more M6PR analogs include one or more malonate M6P analogs having the following structure (where $M^+$ is any countercation or hydrogen atom):

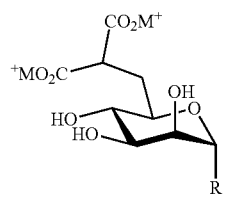

Details regarding M6P and M6P analog recognition by M6PR, as well as M6P analogs that may be employed in the bifunctional molecules of the present disclosure may be found, e.g., in Gary-Bobo et al. (2007) *Curr. Med. Chem.* 14:2945-2953; and Jeanjean et al. (2008) *Bioorg Med Chem Lett.* 18(23): 6240-3, the disclosures of which are incorporated herein by reference in their entireties for all purposes.

In certain aspects, when the second moiety includes one or more M6PR ligands, the second moiety includes from 1 to 1000 M6PR ligands, such as from 1 to 750, 1 to 500, 1 to 250, 1 to 100, 1 to 75, 1 to 50, 1 to 40, 1 to 30, 1 to 20, 1 to 10 (e.g., 1 to 6), or 1 to 5 M6PR ligands. In some embodiments, when the second moiety includes one or more M6PR ligands, the second moiety includes from 10 to 50, 15 to 45, 20 to 40, or 25 to 35 M6PR ligands. In certain aspects, when the second moiety includes one or more M6PR ligands, the second moiety includes 5 or more, 10 or more, 20 or more, 30 or more, 40 or more, 50 or more, 75 or more, 100 or more, 250 or more, 500 or more, 750 or more, or 1000 or more M6PR, ligands.

In some embodiments, when the second moiety includes one or more M6PR ligands, the second moiety includes a polymer scaffold that displays (e.g., is functionalized with) the one or more M6PR ligands. One example of such a bifunctional molecule and use thereof is schematically illustrated in FIG. 1. In this example, the bifunctional molecule includes an antibody as the first moiety. The antibody may bind either a target extracellular molecule (as shown on the left) or a target cell surface molecule (as shown on the right). The antibody is conjugated to a polymer scaffold that displays M6P ligands (each of which is designated "6P" in FIG. 1). Upon binding of a displayed M6P ligand by a cell surface M6PR, the M6PR shuttles the bifunctional molecule (and bound target molecule) to the lysosome for degradation.

When the second moiety includes a polymer scaffold that displays the one or more M6PR ligands, the polymer scaffold may be a glycopolymer including the one or more M6PR ligands. By way of example, the glycopolymer may be a glycoprotein including one or more amino acids (e.g., natural and/or non-natural amino acids) functionalized with the one or more M6PR ligands. When the glycopolymer is a glycoprotein, the glycoprotein may be a N-carboxyanhydride (NCA)-derived glycoprotein. The ring-opening polymerization (ROP) of NCA monomers is a well-studied route to synthetic polypeptides and polypeptide hybrids that possess a broad range of useful physical properties. In some embodiments, the polymerization is metal-catalyzed. Suitable approaches for large-scale synthesis of α-amino acid-N-carboxyanhydrides are described, e.g., in Semple et al. (2016) *Synthetic Communications* 47(1):53-61.

Figure 2:
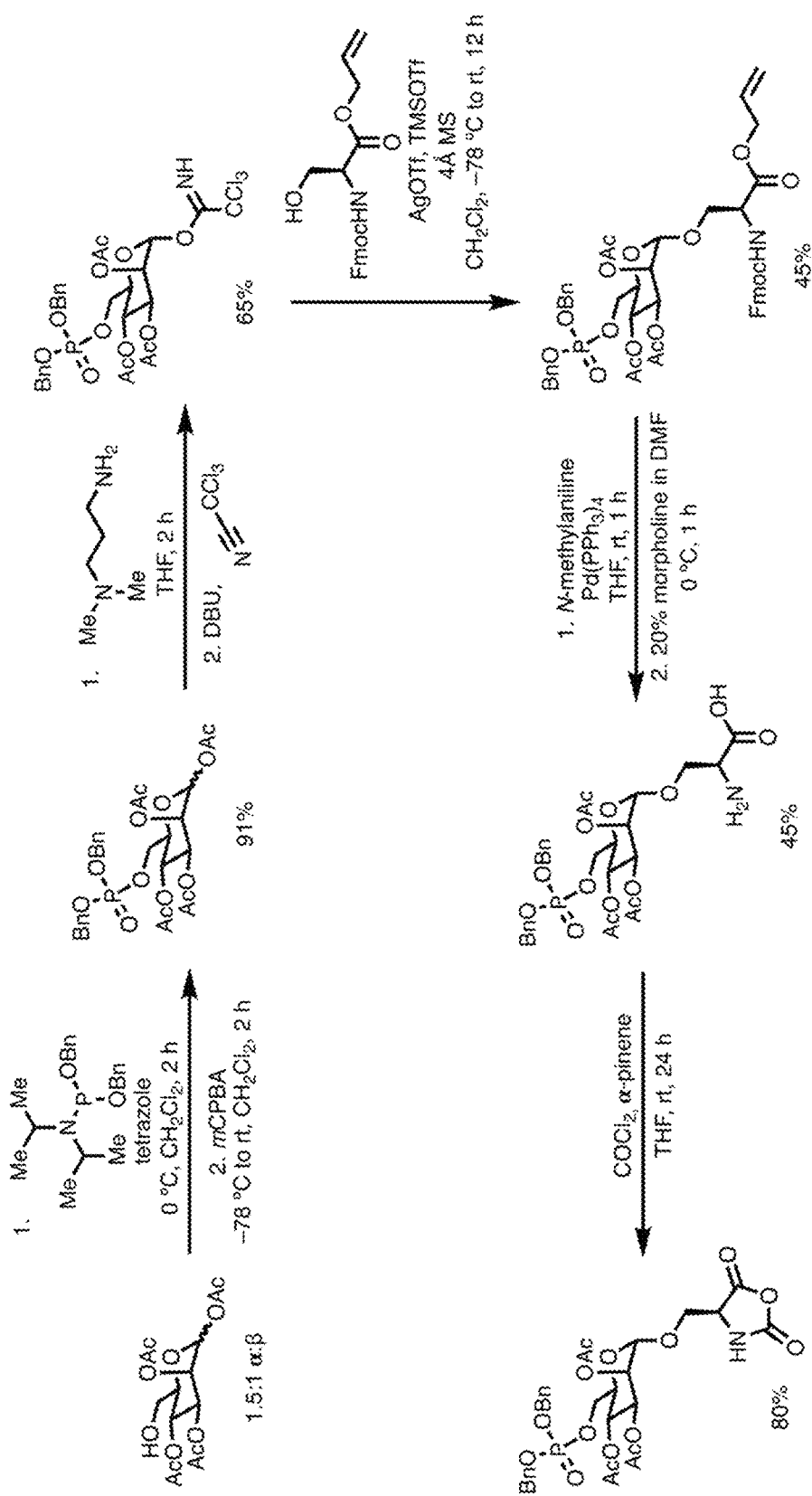
FIG. 2 A scheme for synthesizing mannose-6-phosphate N-carboxyanhydride according to one embodiment. This route allows access to mannose-6-phosphate glycans linked to, e.g., serine residues for use as monomers in N-carboxyanhydride polymerization.
Figure 3:
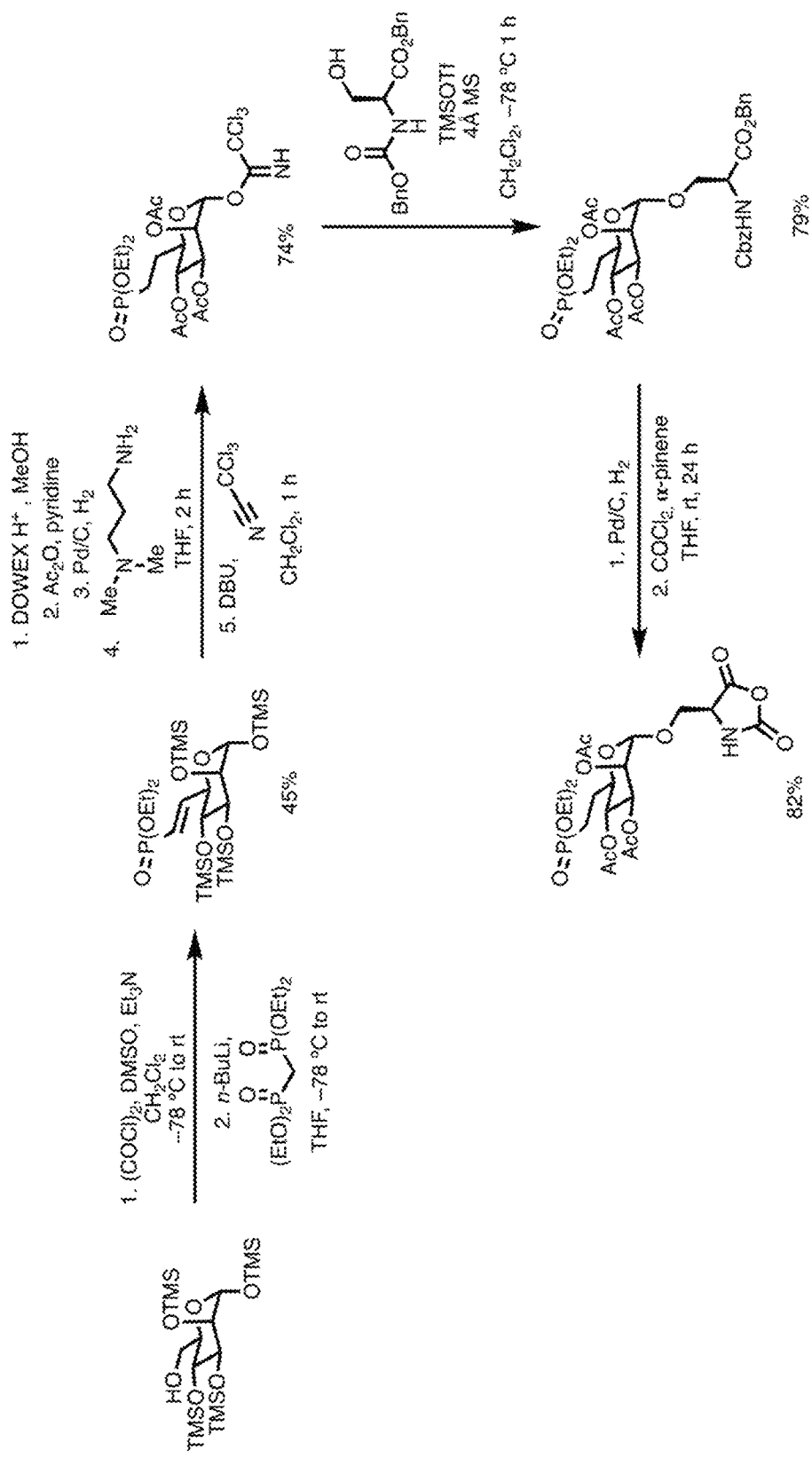
FIG. 3 A scheme for synthesizing mannose-6-phosphonate N-carboxyanhydride according to one embodiment. This route allows access to mannose-6-phosphonate glycans linked to, e.g., serine residues for use as monomers in N-carboxyanhydride polymerization. The phosphonate group is a hydrolytically stable variant of a phosphate group which has previously demonstrated better serum stability compared to mannose-6-phosphate glycans.
Figure 4:
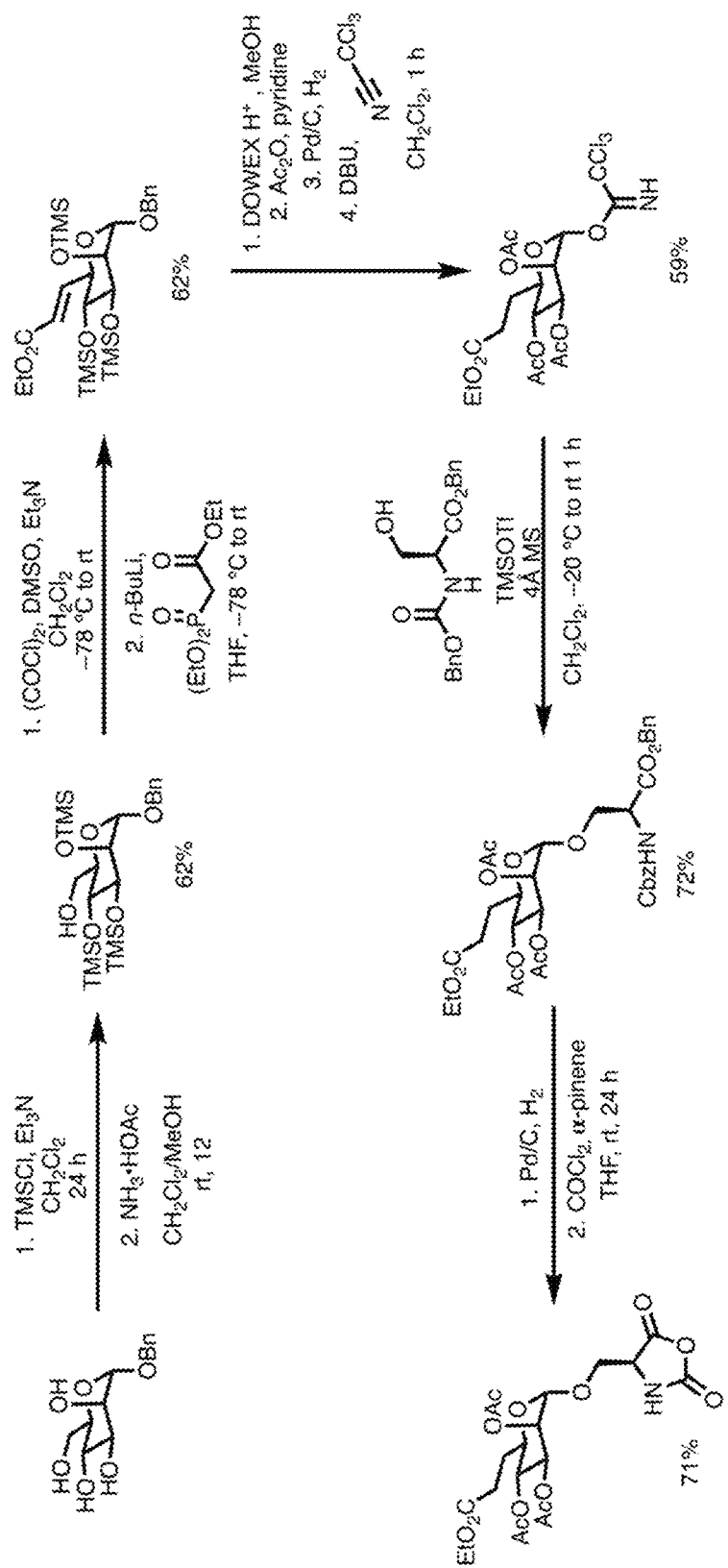
FIG. 4 A scheme for synthesizing mannose-6-carboxylate N-carboxyanhydride according to one embodiment. This route allows access to mannose-6-carboxylate glycans linked to, e.g., serine residues for use as monomers in N-carboxyanhydride polymerization. The carboxylate group is a hydrolytically stable variant of a phosphate group which has previously demonstrated better serum stability compared to mannose-6-phosphate glycans. Mannose-6-carboxylate glycans have previously demonstrated a relative binding affinity of 0.3 for the cation independent M6PR (CIM6PR), compared to mannose-6-phosphate glycans. The ability to chemically tune the receptor-ligand interaction allows for greater control in biological applications to diminish off-target binding events.
Figure 5:
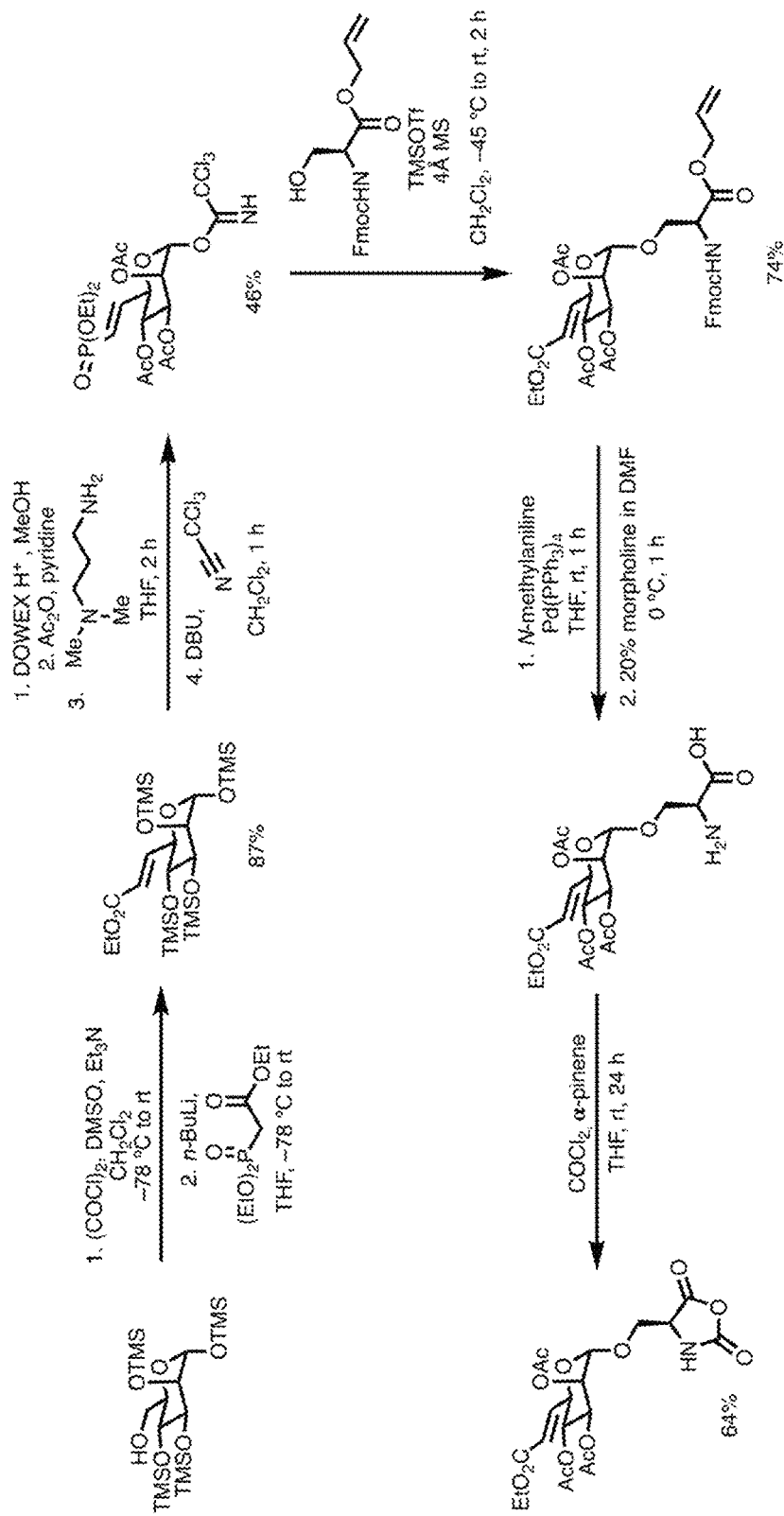
FIG. 5 A scheme for synthesizing mannose-6-acrylate N-carboxyanhydride according to one embodiment. This route allows access to mannose-6-acrylate glycans linked to, e.g., serine residues for use as monomers in N-carboxyanhydride polymerization. The acrylate group is a hydrolytically stable variant of a phosphate group which has previously demonstrated better serum stability compared to mannose-6-phosphate glycans. Mannose-6-acrylate glycans have previously demonstrated a relative binding affinity of 0.7 for the CIM6PR, compared to mannose-6-phosphate glycans. The ability to chemically tune the receptor-ligand interaction allows for greater control in biological applications to diminish off-target binding events.
Figure 6:
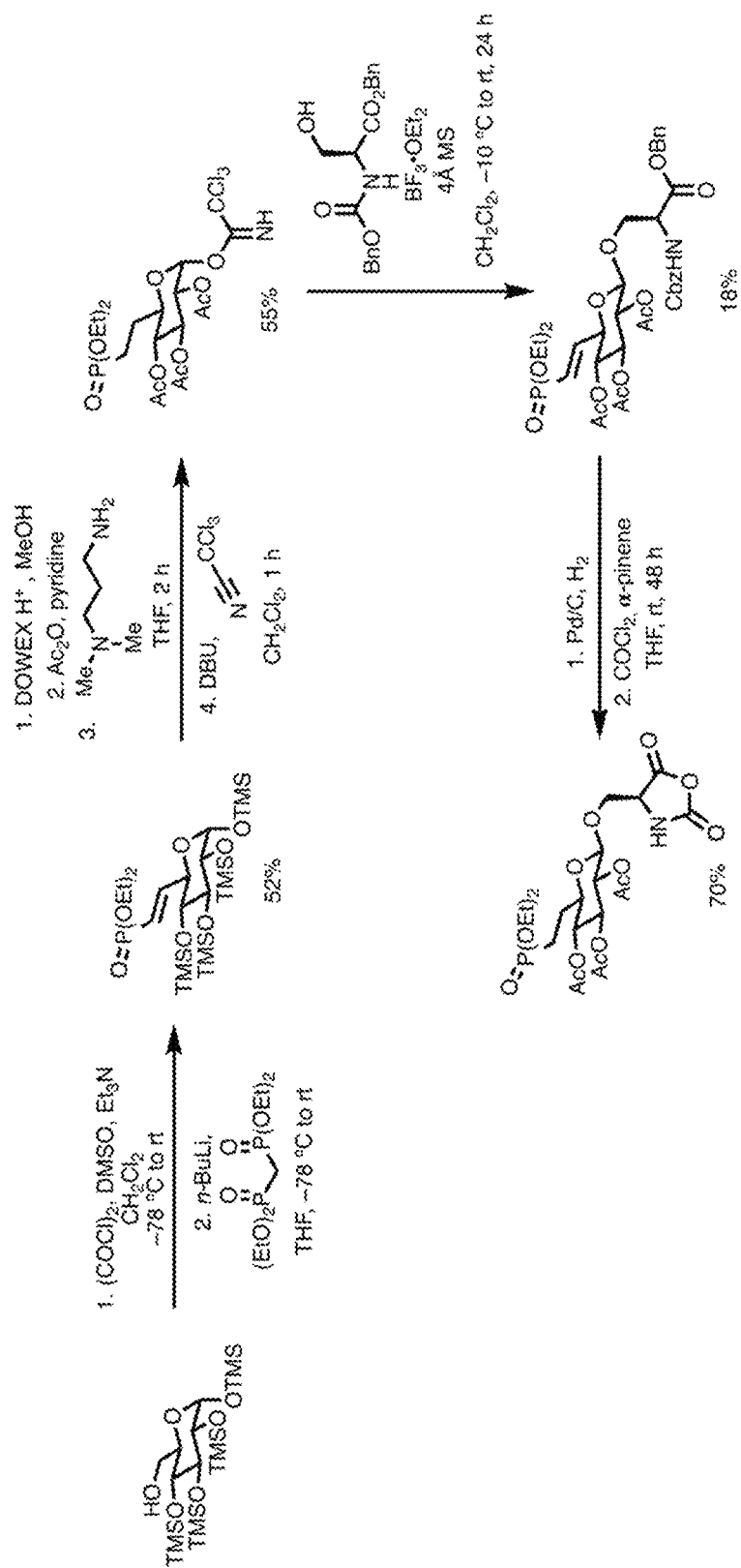
FIG. 6 A scheme for synthesizing glucose-6-phosphonate N-carboxyanhydride according to one embodiment. This route allows access to glucose-6-phosphonate glycans linked to, e.g., serine residues for use as monomers in N-carboxyanhydride polymerization. The glucose-6-phosphonate residue has a significantly weaker binding affinity for the CIM6PR compared to mannose-containing glycans.
Figure 7:
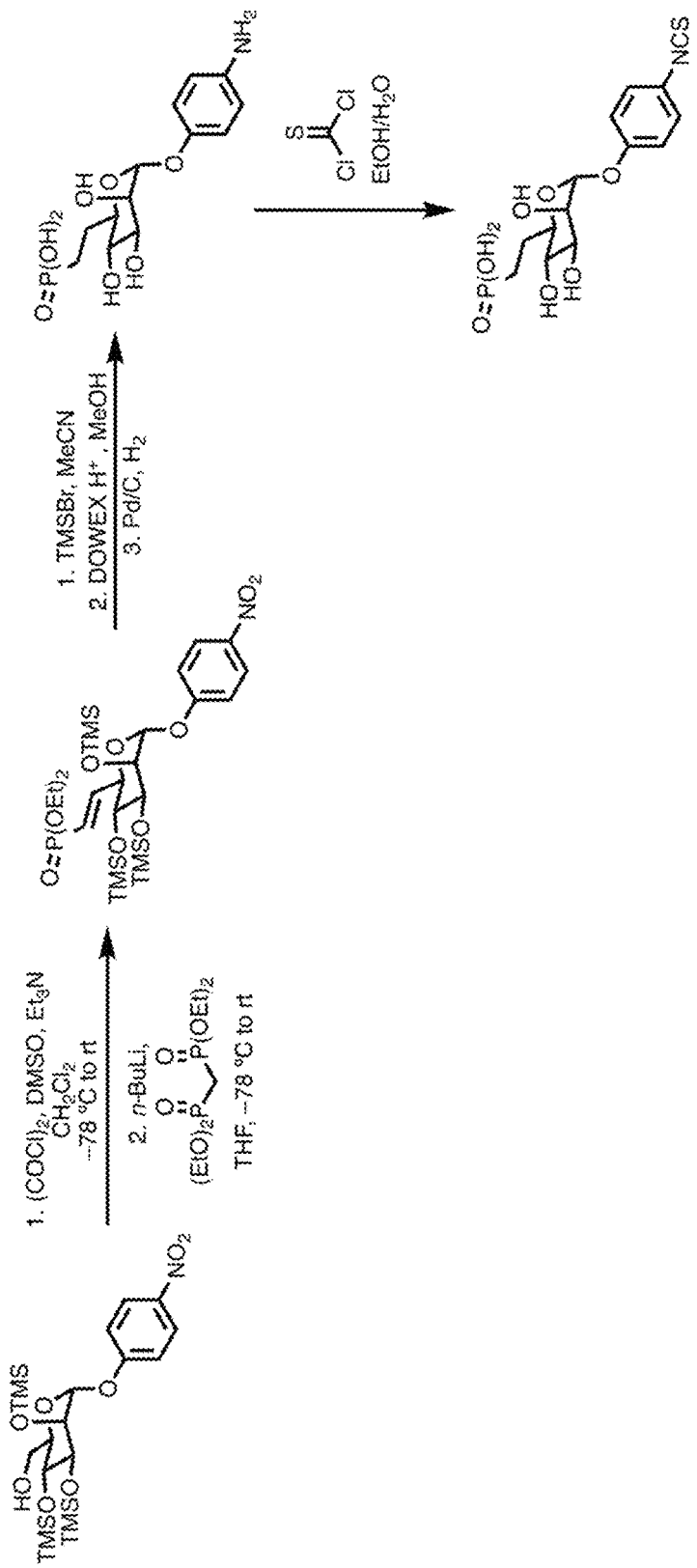
FIG. 7 A scheme for synthesizing mannose-6-phosphonate isothiocyanate according to one embodiment. This route allows access to mannose-6-phosphonate isothiocyanate (M6Pn-ITC), which can be directly conjugated to, e.g., lysine residues in proteins. Conjugation of multiple M6Pn-ITC to multiple amino acids (e.g., lysines) within a given protein allows for multivalent presentation of M6Pn glycans.

An example approach for synthesizing mannose-6-phosphate N-carboxyanhydride is schematically illustrated in FIG. 2. An example approach for synthesizing mannose-6-phosphonate N-carboxyanhydride is schematically illustrated in FIG. 3. An example approach for synthesizing mannose-6-carboxylate N-carboxyanhydride is schematically illustrated in FIG. 4. An example approach for synthesizing mannose-6-acrylate N-carboxyanhydride is schematically illustrated in FIG. 5. An example approach for synthesizing glucose-6-phosphonate N-carboxyanhydride is schematically illustrated in FIG. 6. An example approach for synthesizing mannose-6-phosphonate isothiocyanate is schematically illustrated in FIG. 7.

In certain embodiments, a bifunctional molecule of the present disclosure comprises a second moiety that specifically binds a lysosomal targeting molecule expressed on the surface of liver cells, e.g., hepatocytes (including hepatocellular carcinoma (HCC) cells). A non-limiting example of a lysosomal targeting molecule expressed on the surface of liver cells to which the second moiety may bind is asialoglycoprotein receptor (ASGPR)—a hepatic receptor that mediates removal of glycoconjugates from blood. The receptor comprises two proteins, asialoglycoprotein receptor 1 and 2 (ASGR1 (UniProtKB-P07306-human) and ASGR2 (UniProtKB-P07307-human)), encoded by the genes ASGR1 and ASOR2. ASGPR binds asialoglycoproteins, which are glycoproteins from which a sialic acid has been removed to expose galactose and galactosamine residues. The receptors, which are located on liver cells, remove the target glycoproteins from circulation. ASGPR is highly expressed on the surface of hepatocytes, several human carcinoma cell lines, and liver cancers.

When the lysosomal targeting molecule is ASGPR, suitable second moieties include but are not limited to anti-ASGPR antibodies, ASGPR ligands, and the like. According to some embodiments, such a second moiety comprises one or more ASGPR ligands. Suitable ASGPR ligands include, but are not limited to, one or more N-acetylgalactosamines (GalNAc), one or more galactoses, one or more glucoses, and any combination thereof. In certain embodiments, such a second moiety comprises from 1 to 1000 ASGPR ligands, such as from 1 to 750, 1 to 500, 1 to 250, 1 to 100, 1 to 75, 1 to 50, 1 to 40, 1 to 30, 1 to 20, 1 to 10 (e.g., 1 to 6), or 1 to 5 ASGPR ligands. In some embodiments, when the second moiety includes one or more ASGPR ligands, the second moiety includes from 10 to 50, 15 to 45, 20 to 40, or 25 to 35 ASGPR ligands. In certain embodiments, when the second moiety includes one or more ASGPR ligands, the second moiety includes 3 or more, 5 or more, 10 or more, 20 or more, 30 or more, 40 or more, 50 or more, 75 or more, 100 or more, 250 or more, 500 or more, 750 or more, or 1000 or more ASGPR ligands.

According to some embodiments, when the lysosomal targeting molecule is ASGPR and the second moiety comprises one or more ASGPR ligands, the second moiety comprises a scaffold comprising the one or more ASGPR ligands, in one non-limiting example, the second moiety comprises a polymer comprising GalNAc. In certain embodiments, such a second moiety comprises poly(GalNAc-co-Ala), the structure of which is provided below and in FIG. 20.

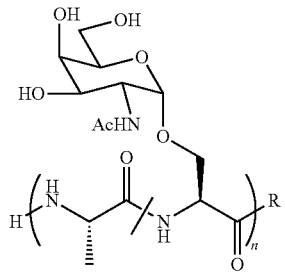

In certain embodiments, when the lysosomal targeting molecule is ASGPR and the second moiety comprises one or more ASGPR ligands, the second moiety comprises a dendrimer scaffold comprising 1 (monovalent), 2 (bivalent), 3 (trivalent) or 4 or more ASGPR ligands, e.g., ASGPR ligands independently selected from GalNAc, galactose, and glucose. For example, according to some embodiments, the second moiety comprises a monovalent, bivalent, or trivalent GalNAc-containing dendrimer scaffold. A non-limiting example of a trivalent GalNAc-containing dendrimer scaffold that may be employed is the following (designated herein as Tri-GalNAc dendrimer):

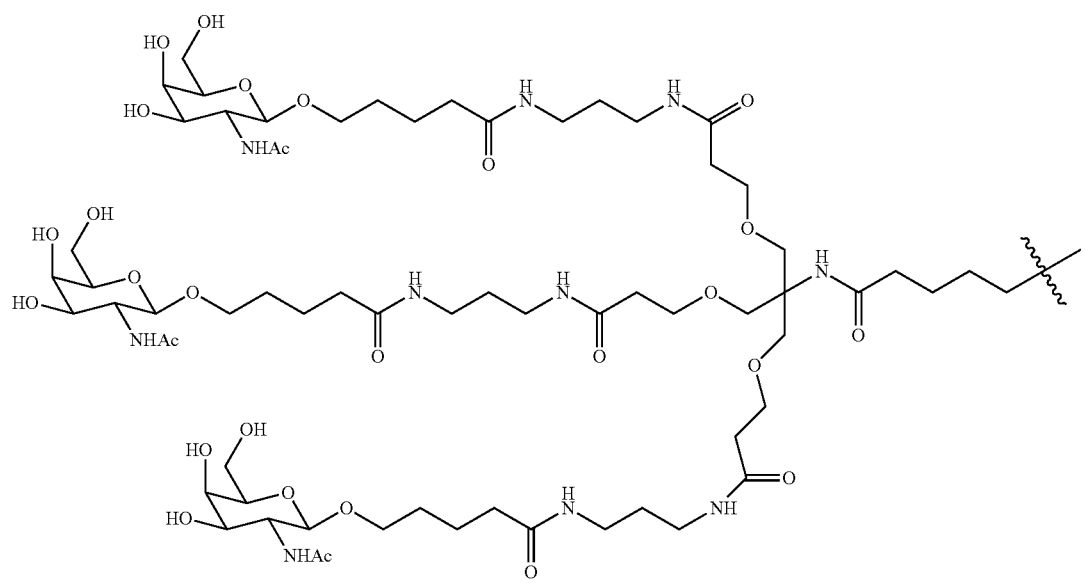 [SMILES: *CCCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]

According to some embodiments, the second moiety comprises a monovalent, bivalent, or trivalent galactose-containing dendrimer scaffold. A non-limiting example of a trivalent galactose-containing dendrimer scaffold that may be employed is the following (designated herein as Tri-Gal dendrimer):

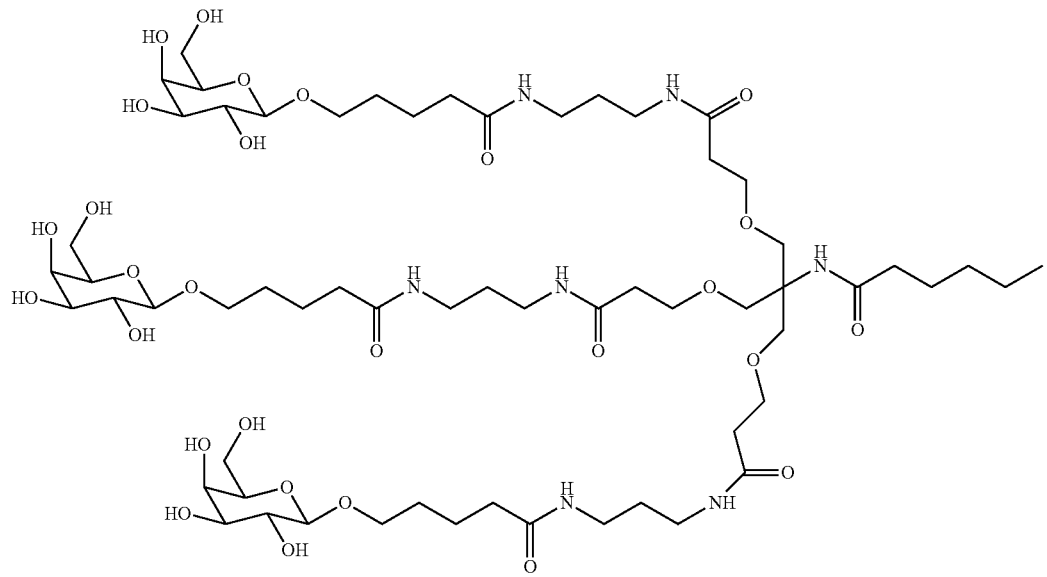 [SMILES: CCCCCC(=O)NC(COCCC(=O)NCCCNC(=O)CCCCOC1OC(CO)C(O)C(O)C1O)(COCCC(=O)NCCCNC(=O)CCCCOC1OC(CO)C(O)C(O)C1O)COCCC(=O)NCCCNC(=O)CCCCOC1OC(CO)C(O)C(O)C1O]

According to some embodiments, when the second moiety specifically binds a lysosomal targeting molecule expressed on the surface of liver cells, e.g., ASGPR, the first moiety specifically binds to a cell surface molecule expressed on hepatocytes (including hepatocellular carcinoma (HCC) cells). Non-limiting examples of such cell surface molecules include growth factor receptors. Growth factor receptors of interest include, but are not limited to, epidermal growth factor receptor (EGFR), C-Met, insulin like growth factor 1 receptor (IGF1R), fibroblast growth factor receptor 4 (FGFR4), HER2, and platelet-derived growth factor receptor (PDGFR).

In certain embodiments, the bifunctional molecule finds use in degrading a growth factor on the surface of hepatocellular carcinoma (HCC) cells (e.g., in vivo upon administration to an individual having HCC to treat the HCC), where the bifunctional molecule comprises a first moiety that specifically binds to EGFR, C-Met, IGF1R, FGFR4 or HER2, and the second moiety specifically binds to ASGPR (e.g., the second moiety may comprise a scaffold (e.g., a polymer scaffold) comprising ASGPR ligands, e.g., GalNAc, galactose, and/or glucose).

According to some embodiments, the bifunctional molecule finds use in degrading a cell surface molecule (e.g., growth factor) expressed on fibrotic liver cells (e.g., in vivo upon administration to an individual having fibrosis of the liver), where the bifunctional molecule comprises a first moiety that specifically binds a cell surface or extracellular protein that promotes fibrosis (e.g., PDGFR), and the second moiety specifically binds to ASGPR (e.g., the second moiety may comprise a scaffold (e.g., a polymer scaffold) comprising one or more ASGPR ligands, e.g., GalNAc, galactose, and/or glucose).

In certain embodiments, the bifunctional molecule enhances degradation of the cell surface molecule or extracellular molecule relative to degradation of the cell surface molecule or extracellular molecule in the presence of the first moiety alone. According to some embodiments, the bifunctional molecule enhances degradation of the cell surface molecule or extracellular molecule relative to degradation of the cell surface molecule or extracellular molecule in the presence of the first moiety or the second moiety alone. By "enhances degradation" in this context means the cell surface molecule or extracellular molecule is degraded in the presence of the bifunctional molecule and is not degraded in the presence of the first moiety alone, or the presence of the first moiety or second moiety alone, under the same conditions; or the cell surface molecule or extracellular molecule is degraded in the presence of the bifunctional molecule to a greater extent than the cell surface molecule or extracellular molecule is degraded in the presence of the first moiety alone, or the presence of the first moiety or second moiety alone, under the same conditions. When the cell surface molecule or extracellular molecule is degraded in the presence of the bifunctional molecule to a greater extent than the cell surface molecule or extracellular molecule is degraded in the presence of the first moiety alone, or the presence of the first moiety or second moiety alone under the same conditions, the degradation may be 1.2 fold or greater, 1.4 fold or greater, 1.6 fold or greater, 1.8 fold or greater, 2 fold or greater, 2.5 fold or greater, 3 fold or greater, 3.5 fold or greater, 4 fold or greater, 4.5 fold or greater, 5 fold or greater, 5.5 fold or greater, 6 fold or Greater, 6.5 fold or greater, 7 fold or greater, 7.5 fold or greater, 8 fold or greater, 8.5 fold or greater, 9 fold or greater, 9.5 fold or greater, or 10 fold or greater in the presence of the bifunctional molecule.

A non-limiting example in which a bifunctional molecule of the present disclosure enhances degradation of a cell surface molecule relative to degradation of the cell surface molecule in the presence of the first moiety alone is provided in Example 4 of the Experimental section below. An example of a bifunctional molecule that does not enhance degradation of a cell surface molecule relative to degradation of the cell surface molecule in the presence of the first moiety alone is provided in Example 5.

One of ordinary skill in the art can readily determine whether a bifunctional molecule of interest enhances degradation of a cell surface molecule or extracellular molecule relative to degradation of the cell surface molecule or extracellular molecule in the presence of the first moiety alone, or in the presence of the first moiety or second moiety alone. Non-limiting examples of suitable approaches for readily making such a determination are provided in the Experimental section below.

A bifunctional molecule of the present disclosure may be in any suitable format. In some embodiments, the first moiety is a polypeptide, the second moiety is a polypeptide, and the bifunctional molecule is a fusion protein comprising the first moiety fused to the second moiety. The first moiety may be fused directly to the second moiety. In other aspects, the first moiety may be fused indirectly to the second moiety, e.g., where a spacer domain is disposed between the first and second moieties. Also provided by the present disclosure are nucleic acids that encode the bifunctional molecule when the bifunctional molecule is a fusion protein. Expression vectors that include such nucleic acids are also provided, as are cells (e.g., host cells) that include any of the nucleic acids and/or expression vectors of the present disclosure. Also provided are methods of producing such cells, the methods including introducing into a cell any of the nucleic acids and/or expression vectors of the present disclosure, e.g., using a suitable cell transfection protocol and transfection reagents. Also provided by the present disclosure are methods of making the bifunctional molecule when the bifunctional molecule is a fusion protein. Such methods may include culturing a cell of the present disclosure under conditions in which the bifunctional molecule is expressed in the cell.

Figure 12:
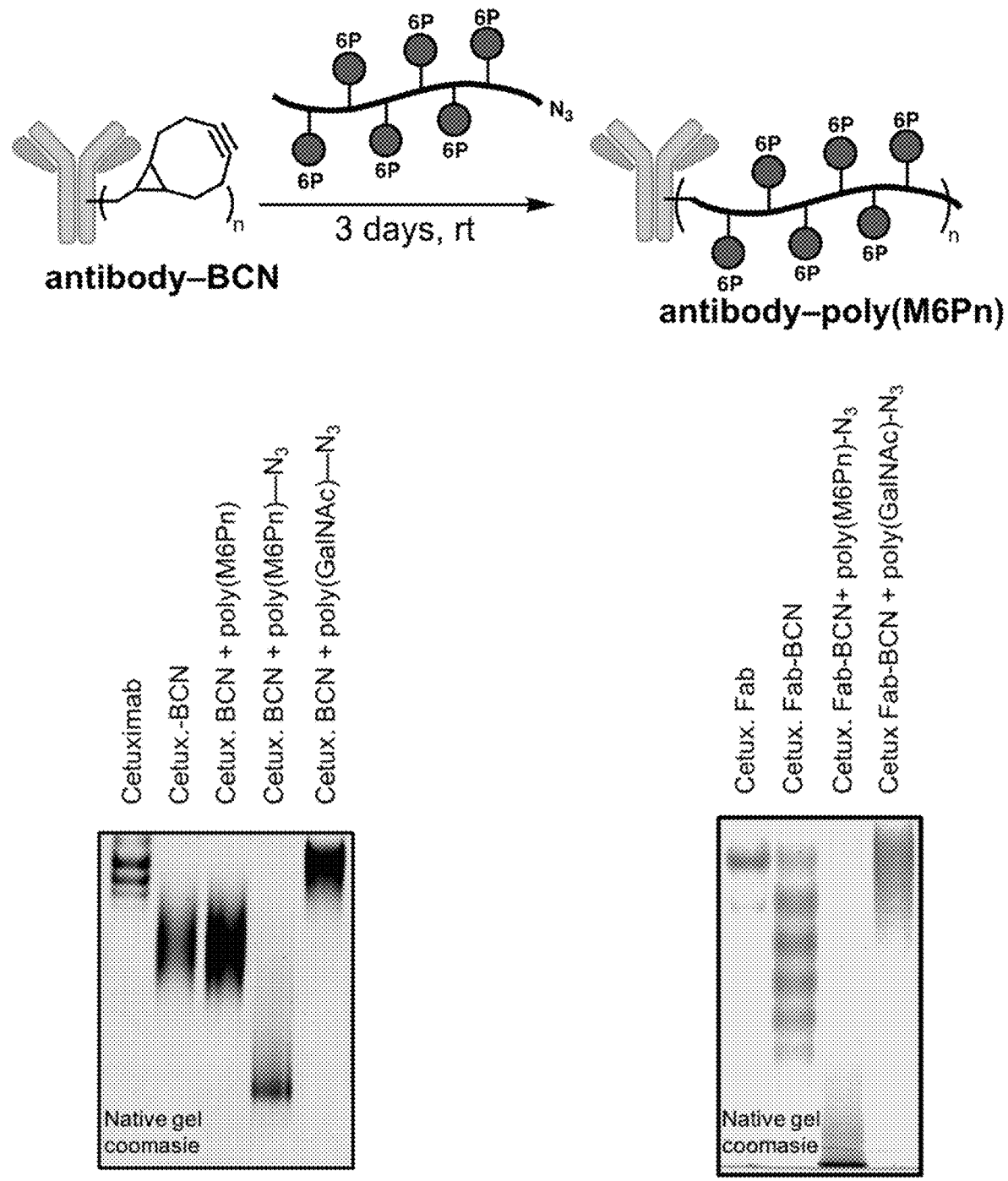
FIG. 12 Data demonstrating that native gel polyacrylamide gel electrophoresis (PAGE) can be used to monitor functionalization of proteins (including antibodies) by M6P polymers. In this example, functionalizations were carried out by first labeling the protein of interested with a reactive alkyne (e.g., bicyclo[6.1.0]nonyne, BCN), followed by incubation with an azide-containing polymer (a bio-orthogonal copper-free strain-promoted click reaction).

Other suitable formats for the bifunctional molecules of the present disclosure include conjugates. Accordingly, in some embodiments, a bifunctional molecule of the present disclosure includes the first moiety conjugated to the second moiety. In certain aspects, the first moiety is an antibody and the second moiety specifically binds M6PR. By way of example, the first moiety may be an antibody and the second moiety may include a polymer scaffold that includes/displays one or more M6PR ligands, e.g., one or more M6Ps and/or M6P analogs, where the polymer scaffold is conjugated to the antibody. In some such embodiments, the second moiety is a glycoprotein including one or more amino acids functionalized with the one or more M6PR ligands. Methods of making such conjugates are also provided, the methods including conjugating the first moiety to the second moiety. A non-limiting example of such a method, where the first moiety is an antibody and the second moiety is a glycopolymer as described herein, is schematically illustrated in FIG. 12. In some embodiments, the methods include site-specifically conjugating the first moiety to the second moiety. For example, when the first moiety includes a polypeptide (e.g., an antibody), the conjugating may include site-specifically conjugating the second moiety to a pre-selected amino acid of the first moiety. In certain aspects, the pre-selected amino acid is at the N-terminus or C-terminus of the first moiety. In other aspects, the pre-selected amino acid is internal to the first moiety—that is, between the N-terminal and C-terminal amino acid of the first moiety. In some embodiments, the pre-selected amino acid is a non-natural amino acid. Non-limiting examples of non-natural amino acids which may be provided to the first and/or second moieties to facilitate conjugation include those having a functional group selected from an azide, alkyne, alkene, amino-oxy, hydrazine, aldehyde (e.g., formylglycine, e.g., SMARTag™ technology from Catalent Pharma Solutions), nitrone, nitrile oxide, cyclopropene, norbornene, iso-cyanide, aryl halide, and boronic acid functional group. Unnatural amino acids which may be incorporated and selected to provide a functional group of interest are known and described in, e.g., Maze et al. (2015) *Bioconjug. Chem.* 26(9):1884-9; Patterson et al. (2014) *ACS Chem. Biol.* 9:592-605; Adumeau et al. (2016) *Mol. Imaging Biol.* (2)153-65; and elsewhere.

In some embodiments, conjugating the first moiety to the second moiety includes conjugating the second moiety to a glycan on the first moiety, or vice versa. Such a method may include modifying one or more glycans on the first moiety to provide a functional group to which the second moiety may be attached. In one non-limiting example, N-glycans on the first moiety (e.g., an antibody) may be modified via periodate oxidation to aldehyde groups, which could then be functionalized with the second moiety, e.g., aminooxy M6Pn.

When the bifunctional molecule is a conjugate, one or more linkers may be employed to facilitate conjugation of the first moiety to the second moiety. Non-limiting examples of such linkers include ester linkers, amide linkers, maleimide or maleimide-based linkers; valine-citrulline linkers; hydrazone linkers; N-succinimidyl-4-(2-pyridyldithio)butyrate (SPDB) linkers; Succinimidyl-4-(N-maleimidomethyl)cyclohexane-1-carboxylate (SMCC) linkers; vinylsulfone-based linkers; linkers that include polyethylene glycol (PEG), such as, but not limited to tetraethylene glycol; linkers that include propanols acid; linkers that include caproleic acid, and linkers including any combination thereof. In certain aspects, the linker is a chemically-labile linker, such as an acid-cleavable linker that is stable at neutral pH (bloodstream pH 7.3-7.5) but undergoes hydrolysis upon internalization into the mildly acidic endosomes (pH 5.0-6.5) and lysosomes (pH 4.5-5.0) of a target cell (e.g., a cancer cell). Chemically-labile linkers include, but are not limited to, hydrazone-based linkers, oxime-based linkers, carbonate-based linkers, ester-based linkers, etc. According to certain embodiments, the linker is an enzyme-labile linker, such as an enzyme-labile linker that is stable in the bloodstream but undergoes enzymatic cleavage upon internalization into a target cell, e.g., by a lysosomal protease (such as cathepsin or plasmin) in a lysosome of the target cell (e.g., a cancer cell). Enzyme-labile linkers include, but are not limited to, linkers that include peptidic bonds, e.g., dipeptide-based linkers such as valine-citrulline linkers, such as a maleimidocaproyl-valine-citruline-p-aminobenzyl (MC-vc-PAB) linker, a valyl-alanyl-para-aminobenzyloxy (Val-Ala-PAB) linker, and the like. Chemically-labile linkers, enzyme-labile, and non-cleavable linkers are known and described in detail, e.g., in Ducry & Stump (2010) *Bioconjugate Chem.* 21:5-13.

Numerous strategies are available for conjugating the first and second moieties through a linker. For example, the first moiety may be derivatized by covalently attaching the linker to the first moiety, where the linker has a functional group capable of reacting with a "chemical handle" on the second moiety. Also by way of example, the second moiety may be derivatized by covalently attaching the linker to the second moiety, where the linker has a functional group capable of reacting with a "chemical handle" on the first moiety. The functional group on the linker may vary and may be selected based on compatibility with the chemical handle on the first or second moiety. According to one embodiment, the chemical handle is provided by incorporation of an unnatural amino acid having the chemical handle into the first or second moiety. In some embodiments, conjugating the first and second moieties is by alkyne-azide cycloaddition.

Figure 19:
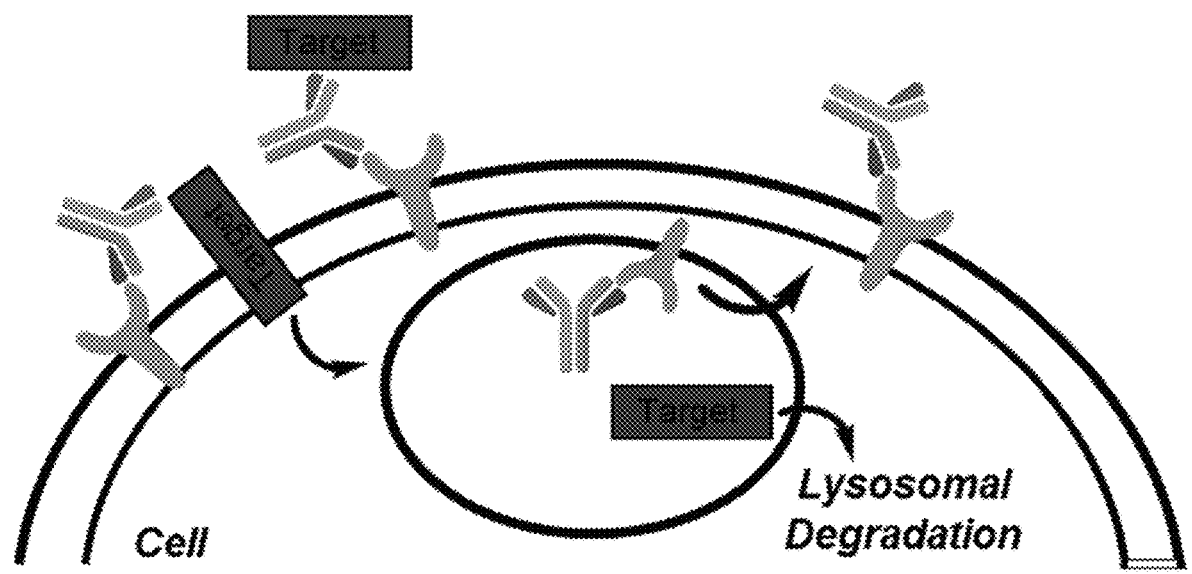
FIG. 19 Schematic illustration of targeted extracellular protein degradation using a bifunctional molecule which is a bispecific antibody. In this example, a bispecific antibody against the CIM6PR and a given target, which disengages from the target at the lowered pH of the endosomes. This strategy allows for a given bispecific antibody to cycle with the receptor and continuously delivery cargo and targets to the lysosome, without degradation of the antibody.

Other suitable formats for the bifunctional molecules of the present disclosure include bispecific antibodies. For example, a bifunctional molecule of the present disclosure may be a bispecific antibody where the first moiety (e.g., a first Fab arm) specifically binds a cell surface molecule or extracellular molecule, and the second moiety (e.g., a second Fab arm) specifically binds a lysosomal targeting molecule (e.g., M6PR). A schematic illustration of such a bispecific antibody is provided in FIG. 19. In some embodiments, the bispecific antibody disengages from the target at the lowered pH of the endosomes. Such a strategy allows for a given bispecific antibody to cycle with the receptor and continuously deliver cargo and targets to the lysosome, without degradation of the antibody. Approaches for making bispecific antibodies are known. For example, when the bifunctional molecule is a bispecific antibody, the bispecific antibody may be made using a "knobs-into-holes" (KIHs) approach. KIHs technology involves engineering CH3 domains to create either a "knob" or a "hole" in each heavy chain to promote heterodimerization. KIHs design and production strategies are known and include those described, e.g., in Xu et al. (2015) *MAbs* 7(1):231-42; Carter et al. (2001) *J. Immunol. Methods* 248(1-2):7-15; Ridgway et al, (1996) *Protein Eng.* 9(7):617-2; and Merchant et al. (1998) *Nat. Biotechnol.* 16(7):677-81.

Compositions

As summarized above, the present disclosure provides compositions. The compositions may include any of the bifunctional molecules of the present disclosure, including any of the bifunctional molecules described in the Bifunctional Molecule section above, which is incorporated but not reiterated herein for purposes of brevity.

In certain aspects, the compositions include a bifunctional molecule of the present disclosure present in a liquid medium. The liquid medium may be an aqueous liquid medium, such as water, a buffered solution, and the like. One or more additives such as a sat (e.g., NaCl, MgCl$_2$, KCl, MgSO$_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.), a protease inhibitor, glycerol, and the like may be present in such compositions.

Pharmaceutical compositions are also provided. The pharmaceutical compositions include any of the bifunctional molecules of the present disclosure, and a pharmaceutically-acceptable carrier. The pharmaceutical compositions generally include a therapeutically effective amount of the bifunctional molecule. By "therapeutically effective amount" is meant a dosage sufficient to produce a desired result, e.g., an amount sufficient to effect beneficial or desired therapeutic (including preventative) results, such as a reduction in cellular proliferation in an individual having a cell proliferative disorder (e.g., cancer) associated with the cell surface molecule or extracellular molecule to which the first moiety of the bifunctional molecule specifically binds, etc. An effective amount may be administered in one or more administrations.

A bifunctional molecule of the present disclosure can be incorporated into a variety of formulations for therapeutic administration. More particularly, the bifunctional molecule can be formulated into pharmaceutical compositions by combination with appropriate pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the bifunctional molecules of the present disclosure suitable for administration to an individual (e.g., suitable for human administration) are generally sterile and may further be free of detectable pyrogens or other contaminants contraindicated for administration to an individual according to a selected route of administration.

In pharmaceutical dosage forms, the bifunctional molecule can be administered alone or in appropriate association, as well as in combination, with other pharmaceutically-active compounds. The following methods and excipients are merely examples and are in no way limiting.

For oral preparations, the bifunctional molecule can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The bifunctional molecules can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The pharmaceutical composition may be in a liquid form, a lyophilized form or a liquid form reconstituted from a lyophilized form, where the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the bifunctional molecule may be prepared in a pH-buffered solution, e.g., at pH ranging from about 4.0 to about 8.0, such as from about 4.5 to about 7.5, e.g., from about 5.0 to about 7.0. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

Methods of Use

As summarized above, also provides are methods of using the bifunctional molecules of the present disclosure. In some embodiments, the methods including using any of the bifunctional molecules described in the Bifunctional Molecule section above, which is incorporated but not reiterated herein for purposes of brevity.

In certain aspects, provided are methods of degrading a cell surface molecule or extracellular molecule. Such methods include contacting the cell surface molecule or extracellular molecule with any of the bifunctional molecules of the present disclosure, under conditions in which the lysosomal targeting molecule shuttles the cell surface molecule or extracellular molecule to the lysosome for degradation. Such methods find use in a variety of applications. In certain aspects, the method is performed in vitro (e.g., in a tube, cell culture plate or well, or the like) and finds use, e.g., in testing and/or research applications. In other aspects, the method is performed in vivo (e.g., in an individual to whom the bifunctional molecule is administered) and finds use, e.g., in clinical/therapeutic applications.

In some embodiments, provided are methods that include administering to an individual in need thereof a therapeutically effective amount of any of the bifunctional molecules or any of the pharmaceutical compositions of the present disclosure. A variety of individuals are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual is a human.

In some embodiments, an effective amount of the bifunctional molecule (or pharmaceutical composition including same) is an amount that, when administered alone (e.g., in monotherapy) or in combination (e.g., in combination therapy) with one or more additional therapeutic agents, in one or more doses, is effective to reduce the symptoms of a medical condition of the individual (e.g., cancer, neurodegenerative disorder, etc.) by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the bifunctional molecule or pharmaceutical composition.

In certain aspects, the individual has, or is suspected of having a neurodegenerative disorder characterized by amyloid-β deposition in the brain (e.g., Alzheimer's Disease) or tau protein deposition in the brain (e.g., a tauopathy), and the first moiety of the bifunctional molecule specifically binds to apoE4 (e.g., apoE4 expressed from the ε4 allele of the APOE4 gene), such that targeted degradation of apoE4 treats the individual's neurodegenerative disorder.

In some embodiments, provided are methods that include administering to an individual having cancer a therapeutically effective amount of any of the bifunctional molecules or any of the pharmaceutical compositions of the present disclosure. According to such methods, the first moiety of the bifunctional molecule specifically binds a cell surface molecule or extracellular molecule that at least contributes to individual's cancer, and where targeted degradation of the cell surface molecule or extracellular molecule using the bifunctional molecule treats the individual's cancer. In certain aspects, the first moiety specifically binds to a molecule selected from a cell surface molecule on a cancer cell, a ligand for a cell surface molecule on a cancer cell, a cell surface molecule on an immune cell, a ligand for a cell surface molecule on an immune cell, an inhibitory immune receptor, and a ligand of an inhibitory immune receptor.

In certain embodiments, the individual has a cancer characterized by the presence of a solid tumor, a semi-solid tumor, a primary tumor, a metastatic tumor, or the like. In some embodiments, the individual has a cancer selected from breast cancer, melanoma, lung cancer, colorectal cancer, prostate cancer, glioma, bladder cancer, endometrial cancer, kidney cancer, leukemia (e.g., acute myeloid leukemia (AML)) liver cancer (e.g., hepatocellular carcinoma (HCC), such as primary or recurrent HCC), non-Hodgkin lymphoma, pancreatic cancer, thyroid cancer, any combinations thereof, and any sub-types thereof.

According to some embodiments, the individual has a particular liver disease (including; but not limited to hepatocellular carcinoma (HCC)), and the methods are for treating the disease. For example, in certain embodiments, the individual has HCC, the first moiety binds a cell surface molecule on HCC cells of the individual, and the second moiety binds ASGPR. In certain embodiments, the first moiety binds a tumor-promoting protein on HCC cells of the individual. According to some embodiments, the tumor-promoting protein is a growth factor on the HCC cells. Non-limiting examples of such growth factors include EGFR, C-Met, IGF1R, and FGFR4. Such a bifunctional molecule may include any of the second moieties that bind ASGPR as described elsewhere herein.

In certain embodiments, the individual has fibrosis of the liver, and the methods are for treating the liver fibrosis. For example, according to some embodiments, the individual has liver fibrosis, the first moiety binds a cell surface molecule on fibrotic liver cells of the individual, and the second moiety binds ASGPR. In certain embodiments, the first moiety binds a fibrosis-promoting protein on the fibrotic liver cells of the individual. According to some embodiments, the fibrosis-promoting protein is a growth factor on the fibrotic liver cells. A non-limiting example of such a growth factor is PDGFR. Such a bifunctional molecule may include any of the second moieties that bind ASGPR as described elsewhere herein.

In any of the methods of using the bifunctional molecules of the present disclosure, in certain embodiments, the bifunctional molecule enhances degradation of the cell surface molecule or extracellular molecule relative to degradation of the cell surface molecule or extracellular molecule in the presence of the first moiety alone. Similarly, in any of the methods of using the bifunctional molecules of the present disclosure, according to some embodiments, the bifunctional molecule enhances degradation of the cell surface molecule or extracellular molecule relative to degradation of the cell surface molecule or extracellular molecule in the presence of the first moiety or the second moiety alone. Details regarding such enhancement of degradation are provided in the Bifunctional Molecules section above and incorporated but not reiterated herein for purposes of brevity.

By "treat", "treating" or "treatment" is meant at least an amelioration of the symptoms associated with the medical condition (e.g., cell proliferative disorder, e.g., cancer) of the individual, where amelioration is used in a broad sense to refer to at least a reduction in the magnitude of a parameter, e.g. symptom, associated with the medical condition being treated. As such, treatment also includes situations where the medical condition, or at least symptoms associated therewith, are completely inhibited, e.g., prevented from happening, or stopped, e.g., terminated, such that the individual no longer suffers from the medical condition, or at least the symptoms that characterize the medical condition.

In certain aspects, the present disclosure provides methods of enhancing antibody-dependent cellular cytotoxicity (ADCC) including administering to an individual in need of ADCC a bifunctional molecule or pharmaceutical composition of the present disclosure. In some embodiments, the first moiety of the bifunctional molecule specifically binds to an inhibitory immune receptor or a ligand of an inhibitory immune receptor. In certain aspects, the first moiety of the bifunctional molecule specifically binds to an immune checkpoint molecule such as PD-1 PD-L1, CTLA4, TIM3, LAG3, TIGIT, or a member of the B7 family.

The bifunctional molecule or pharmaceutical composition may be administered to the individual using any available method and route suitable for drug delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. In some embodiments, the administering is by parenteral administration. Routes of administration may be combined, if desired, or adjusted depending upon the bifunctional molecule and/or the desired effect. The bifunctional molecules or pharmaceutical compositions may be administered in a single dose or in multiple doses. In some embodiments, the bifunctional molecule or pharmaceutical composition is administered intravenously. In some embodiments, the bifunctional molecule or pharmaceutical composition is administered by injection, e.g., for systemic delivery (e.g., intravenous infusion) or to a local site.

Kits

As summarized above, the present disclosure also provides kits. In some embodiments, a subject kit includes any of the bifunctional molecules of the present disclosure (including any of the bifunctional molecules described in the Bifunctional Molecule section above, which is incorporated but not reiterated herein for purposes of brevity), and instructions for using the bifunctional molecule to degrade the cell surface molecule or extracellular molecule to which the first moiety specifically binds. In certain aspects, the instructions are for degrading the cell surface molecule or extracellular molecule in vitro, e.g., for research and/or testing purposes. In other aspects, the instructions are for degrading the cell surface molecule or extracellular molecule in vivo, e.g., for clinical/therapeutic applications. For example, provided are kits that include any of the bifunctional molecules or pharmaceutical compositions of the present disclosure, and instructions for administering the bifunctional molecule or pharmaceutical composition to an individual in need thereof. Such kits may include a quantity of the bifunctional molecule or pharmaceutical composition, present in unit dosages, e.g., ampoules, or a multi-dosage format. As such, in certain embodiments, the kits may include one or more (e.g., two or more) unit dosages (e.g., ampoules) of the bifunctional molecule or pharmaceutical composition.

The term "unit dosage", as used herein, refers to physically discrete units suitable as unitary dosages for human and animal subjects, each unit containing a predetermined quantity of the composition calculated in an amount sufficient to produce the desired effect. The amount of the unit dosage depends on various factors, such as the particular bifunctional molecule employed, the effect to be achieved, and the pharmacodynamics associated with the bifunctional molecule, in the individual. In yet other embodiments, the kits may include a single multi dosage amount of the bifunctional molecule or pharmaceutical composition.

In other aspects, provided are kits that include any of the glycopolymers of the present disclosure (including any of the glycopolymers described in the Bifunctional Molecule section above, which is incorporated but not reiterated herein for purposes of brevity), and instructions for conjugating the glycopolymer to a molecule of interest. Such kits may further include reagents for conjugating the glycopolymer to a molecule of interest. In some embodiments, the molecule of interest is a polypeptide. Non-limiting examples of such polypeptides include antibodies. In certain aspects, the molecule of interest specifically binds a cell surface molecule or extracellular molecule, including any of the cell surface molecules or extracellular molecules described in the Bifunctional Molecule section above, which is incorporated but not reiterated herein for purposes of brevity.

Components of the kits may be present in separate containers, or multiple components may be present in a single container.

The instructions included in the kits may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the interest, are provided. An example of this embodiment is a kit that includes a web address where the instructions can be viewed and/or from which the instructions can be downloaded. As with the instructions, the means for obtaining the instructions is recorded on a suitable substrate.

Glycopolymers, Monomers, and Methods of Making Same

The present disclosure also provides glycopolymers. In some embodiments, a glycopolymer of the present disclosure includes a polymer scaffold and one or more mannose-6-phosphate receptor (M6PR) ligands attached to the polymer scaffold. The glycopolymer, polymer scaffold, and/or M6PR ligands may be any of those described in the Bifunctional Molecule section above, which is incorporated but not reiterated herein for purposes of brevity. For example, the glycopolymer may be a glycoprotein including one or more amino acids functionalized with the one or more M6PR ligands. The glycoprotein may be a N-carboxyanhydride (NCA)-derived glycoprotein. In certain aspects, the one or more M6PR ligands include one or more mannose-6-phosphates (M6P). Alternatively, or additionally, the one or more M6PR ligands include one or more M6P analogs, e.g., any of the M6P analogs described herein, such as one or more mannose-6-phosphonates (M6Pn). In some embodiments, the polymer scaffold includes from 1 to 50 M6PR ligands, such as from 1 to 40, 1 to 30, 1 to 20, 1 to 10 (e.g., 1 to 6), or 1 to 5 M6PR ligands. In certain aspects, the polymer scaffold includes from 10 to 50, 15 to 45, 20 to 40, or 25 to 35 M6PR ligands. In certain aspects, the polymer scaffold includes 5 or more, 10 or more, 20 or more, 30 or more, or 40 or more M6PR ligands.

Figure 8:
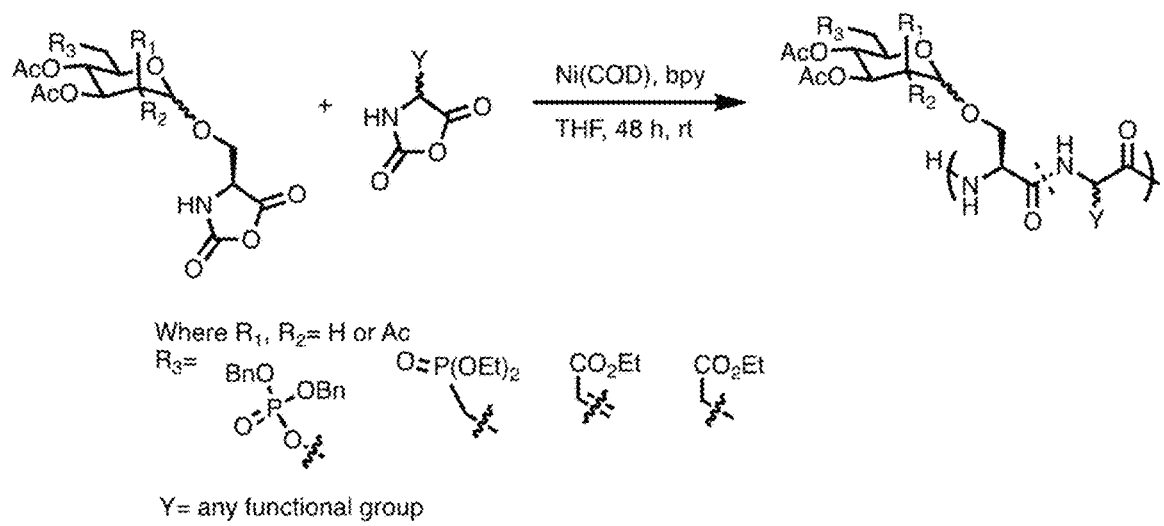
FIG. 8 An illustration of a general NCA polymerization scheme for synthesizing a scaffold for displaying M6P ligands according to one embodiment. Copolymers with other amino-acid derived NCAs are readily synthesized similarly, and provide access to numerous polymers with varied structures and compositions bearing multiple M6P ligand residues. These materials are subsequently deprotected to provide the full polypeptidelglycan structure.
Figure 8:
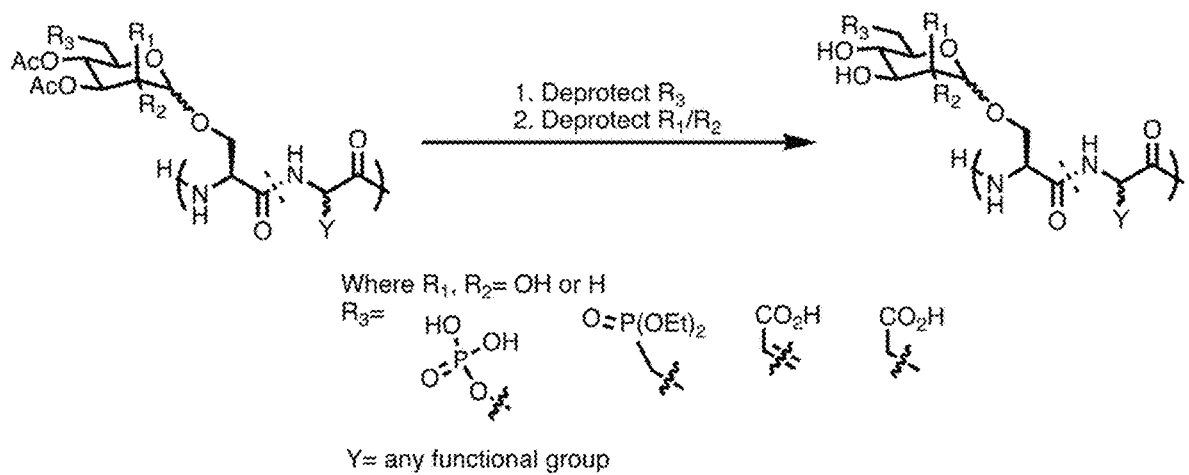

Also provided are methods of making the glycopolymers of the present disclosure. In some embodiments, making the glycopolymer includes polymerization. The polymerization may be by NCA polymerization, an example of which is schematically illustrated in FIG. 8.

Figure 9:
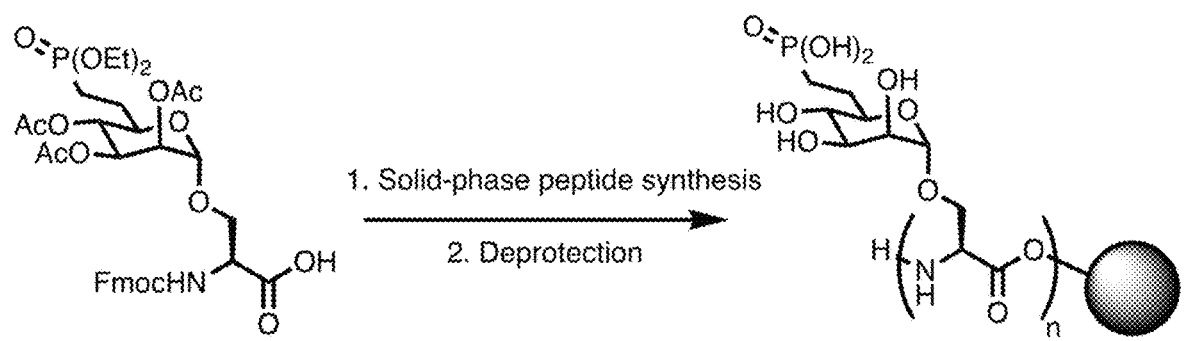
FIG. 9 A scheme for solid-phase peptide synthesis of mannose-6-phosphonate peptide oligomer according to one embodiment. As shown, a scaffold for displaying M6P ligands can also be synthesized using solid-phase peptide synthesis, starting from M6P, M6Pn, etc. amino acids. This synthetic route allows for greater control over polypeptide length and composition compared to the NCA polymerization route, and does not require special synthesis conditions compared to the NCA polymerization-derived materials.

In certain aspects, a method of making the glycopolymer includes attaching the one or more M6PR ligands to the polymer scaffold. In other aspects, such methods include synthesizing the polymer scaffold from monomers functionalized with the one or more M6PR ligands. For example, the scaffold may be synthesized from one or more monomers functionalized with the one or more M6PR ligands, where the synthesizing is by solid-phase synthesis. An example solid-phase synthesis scheme is provided in FIG. 9.

In related aspects, the present disclosure provides monomers. The monomers are functionalized with one or more mannose-6-phosphate receptor (M6PR) ligands. In certain aspects, the monomers are amino adds. In some embodiments, the monomers are non-natural amino adds. The one or more M6PR ligands may include one or more mannose-6-phosphates (M6P). Alternatively, or additionally, the one or more M6PR ligands may include one or more M6P analogs, e.g., any of the M6P analogs described herein, such as mannose-6-phosphonates (M6Pn).

Notwithstanding the appended claims, the present disclosure is also defined by the following embodiments.

1. A bifunctional molecule comprising:
   a first moiety that specifically binds a cell surface molecule or extracellular molecule; and
   a second moiety that specifically binds a lysosomal targeting molecule.
2. The bifunctional molecule of embodiment 1, wherein the bifunctional molecule enhances degradation of the cell surface molecule or extracellular molecule relative to degradation of the cell surface molecule or extracellular molecule in the presence of the first moiety alone.
3. The bifunctional molecule of embodiment 1 or embodiment 2, wherein the first moiety specifically binds a cell surface molecule.
4. The bifunctional molecule of embodiment 3, wherein the cell surface molecule is a cell surface receptor.
5. The bifunctional molecule of embodiment 4, wherein the cell surface receptor is a growth factor receptor.
6. The bifunctional molecule of any one of embodiments 1 to 5, wherein the cell surface molecule is present on a cancer cell.
7. The bifunctional molecule of embodiment 6, wherein the cell surface molecule is a tumor-associated antigen or a tumor-specific antigen.
8. The bifunctional molecule of any one of embodiments 1 to 7, wherein the cell surface molecule is present on an immune cell.
9. The bifunctional molecule of embodiment 8, wherein the immune cell is selected from the group consisting of: a natural killer (NM) cell, a macrophage, a monocyte, a neutrophil, a dendritic cell, a T cell, a B cell, a mast cell, a basophil, and an eosinophil.
10. The bifunctional molecule of embodiment 8, wherein the cell surface molecule is an inhibitory immune receptor.
11. The bifunctional molecule of embodiment 10, wherein the cell surface molecule is a ligand of an inhibitory immune receptor.
12. The bifunctional molecule of embodiment 8, wherein the cell surface molecule is an immune checkpoint molecule.
13. The bifunctional molecule of embodiment 12, wherein the immune checkpoint molecule is selected from the group consisting of: PD-1, PD-L1, CTLA4, TIM3, LAG3, TIGIT, and a member of the B7 family.
14. The bifunctional molecule of embodiment 1, wherein the first moiety specifically binds an extracellular molecule.
15. The bifunctional molecule of embodiment 14, wherein the extracellular molecule is a ligand for a cell surface receptor.
16. The bifunctional molecule of embodiment 15, wherein the extracellular molecule is a growth factor.
17. The bifunctional molecule of embodiment 15, wherein the extracellular molecule is a cytokine or a chemokine.
18. The bifunctional molecule of embodiment 14, wherein the extracellular molecule is an antibody.
19. The bifunctional molecule of embodiment 18, wherein the antibody is an autoantibody.
20. The bifunctional molecule of embodiment 18 or embodiment 19, wherein the antibody specifically binds to a cell surface molecule or an extracellular molecule.
21. The bifunctional molecule of any one of embodiments 1 to 20, wherein the first moiety is selected from the group consisting of: a polypeptide, a ligand, an aptamer, a nanoparticle, and a small molecule.
22. The bifunctional molecule of embodiment 21, wherein the first moiety is a polypeptide.
23. The bifunctional molecule of embodiment 22, wherein the first moiety is an antibody.
24. The bifunctional molecule of embodiment 23, wherein the antibody is an IgG, a single chain Fv (scFv), Fab, $(Fab)_2$, $(scFv')_2$, or a nanobody.
25. The bifunctional molecule of any one of embodiments 1 to 24, wherein the second moiety is selected from the group consisting of: a polypeptide, a ligand, an aptamer, a nanoparticle, and a small molecule.
26. The bifunctional molecule of any one of embodiments 1 to 25, wherein the lysosomal targeting molecule is a mannose-6-phosphate receptor (M6PR).
27. The bifunctional molecule of embodiment 26, wherein the second moiety comprises one or more M6PR ligands.
28. The bifunctional molecule of embodiment 27, wherein the one or more M6PR ligands comprise one or more mannose-6-phosphates (M6P).
29. The bifunctional molecule of embodiment 27 or embodiment 28, wherein the one or more M6PR ligands comprise one or more M6P analogs.
30. The bifunctional molecule of embodiment 29, wherein the one or more M6P analogs comprise one or more mannose-6-phosphonates (M6Pn).
31. The bifunctional molecule of any one of embodiments 27 to 30, wherein the second moiety comprises from 1 to 500 M6PR ligands.
32. The bifunctional molecule of any one of embodiments 27 to 31, wherein the second moiety comprises a polymer scaffold that displays the one or more M6PR ligands.
33. The bifunctional molecule of embodiment 32, wherein the polymer scaffold is a glycopolymer comprising the one or more M6PR ligands.
34. The bifunctional molecule of embodiment 33, wherein the glycopolymer is a glycoprotein comprising one or more amino acids functionalized with the one or more M6PR ligands.
35. The bifunctional molecule of embodiment 34, wherein the glycoprotein is a N-carboxyanhydride (NCA)-derived glycoprotein.
36. The bifunctional molecule of any one of embodiments 1 to 25, wherein the lysosomal targeting molecule is expressed on the surface of liver cells.

37. The bifunctional molecule of embodiment 36, wherein the lysosomal targeting molecule is expressed on the surface of hepatocytes.
38. The bifunctional molecule of embodiment 36 or embodiment 37, wherein the lysosomal targeting molecule is expressed on the surface of hepatocellular carcinoma (HCC) cells, fibrotic liver cells, or both.
39. The bifunctional molecule of any one of embodiments 36 to 38, wherein the lysosomal targeting molecule is asialoglycoprotein receptor (ASGPR).
40. The bifunctional molecule of embodiment 39, wherein the second moiety comprises one or more ASGPR ligands.
41. The bifunctional molecule of embodiment 40, wherein the one or more ASGPR ligands comprises one or more N-acetylgalactosamines (GalNAc).
42. The bifunctional molecule of embodiment 40 or embodiment 41, wherein the one or more ASGPR ligands comprises one or more galactoses.
43. The bifunctional molecule of any one of embodiments 40 to 42, wherein the one or more ASGPR ligands comprises one or more glucoses.
44. The bifunctional molecule of any one of embodiments 40 to 43, wherein the second moiety comprises from 1 to 500 ASGPR ligands.
45. The bifunctional molecule of any one of embodiments 40 to 44, wherein the second moiety comprises a polymer comprising the one or more ASGPR ligands.
46. The bifunctional molecule of embodiment 45, wherein the second moiety comprises poly(GalNAc-co-Ala).
47. The bifunctional molecule of embodiment 41, wherein the second moiety comprises a monovalent, bivalent, or trivalent GalNAc-containing dendrimer scaffold.
48. The bifunctional molecule of embodiment 47, wherein the second moiety comprises a trivalent GalNAc-containing dendrimer scaffold.
49. The bifunctional molecule of embodiment 42, wherein the second moiety comprises a monovalent, bivalent, or trivalent galactose-containing dendrimer scaffold.
50. The bifunctional molecule of embodiment 49, wherein the second moiety comprises a trivalent galactose-containing dendrimer scaffold.
51. The bifunctional molecule of any one of embodiments 36 to 50, wherein the first moiety specifically binds a cell surface molecule expressed on hepatocytes.
52. The bifunctional molecule of embodiment 51, wherein the cell surface molecule is a growth factor receptor.
53. The bifunctional molecule of embodiment 52, wherein the growth factor receptor is selected from the group consisting of epidermal growth factor receptor (EGFR), C-Met, insulin like growth factor 1 receptor (IGF1R), fibroblast growth factor receptor 4 (FGFR4), and platelet-derived growth factor receptor (PDGFR).
54. The bifunctional molecule of any one of embodiments 1 to 53, wherein the first moiety is a polypeptide and the second moiety is a polypeptide, and wherein the bifunctional molecule is a fusion protein comprising the first moiety fused to the second moiety.
55. The bifunctional molecule of embodiment 54, wherein the first moiety is fused directly to the second moiety.
56. The bifunctional molecule of embodiment 54, comprising a spacer domain between the first moiety and the second moiety.
57. The bifunctional molecule of any one of embodiments 1 to 56, wherein the bifunctional molecule is a bispecific antibody that specifically binds:
a cell surface molecule or extracellular molecule; and
a lysosomal targeting molecule.
58. The bifunctional molecule of any one of embodiments 1 to 53, wherein the bifunctional molecule is a conjugate comprising the first moiety conjugated to the second moiety.
59. The bifunctional molecule of embodiment 58, wherein the first moiety is an antibody.
60. The bifunctional molecule of embodiment 58 or embodiment 59, comprising a second moiety as defined in any one of embodiments 27 to 35.
61. The bifunctional molecule of embodiment 58 or embodiment 59, comprising a second moiety as defined in any one of embodiments 40 to 50.
62. A nucleic acid encoding the bifunctional molecule of any one of embodiments 54 to 57.
63. An expression vector comprising the nucleic acid of embodiment 62.
64. A cell comprising the nucleic acid of embodiment 62 or the expression vector of embodiment 63.
65. A method of producing the cell of embodiment 64, comprising introducing into a cell the nucleic acid of embodiment 62 or the expression vector of embodiment 63.
66. A method of making the bifunctional molecule of embodiment 53 or embodiment
59. comprising conjugating the first moiety to the second moiety.
67. The method according to embodiment 66, wherein the conjugating comprises site-specifically conjugating the first moiety to the second moiety.
68. The method according to embodiment 67, wherein the first moiety comprises a polypeptide, and wherein the conjugating comprises site-specifically conjugating the second moiety to a pre-selected amino acid of the first moiety.
69. The method according to embodiment 68, wherein the pre-selected amino acid is at the N-terminus or C-terminus of the first moiety.
70. The method according to embodiment 68, wherein the pre-selected amino acid is internal to the first moiety.
71. The method according to any one of embodiments 68 to 70, wherein the pre-selected amino acid is a non-natural amino acid.
72. The method according to any one of embodiments 66 to 71, wherein the first moiety is an antibody.
73. The method according to any one of embodiments 66 to 72, wherein the second moiety is as defined in any one of embodiments 27 to 35.
74. The method according to any one of embodiments 66 to 72, wherein the second moiety is as defined in any one of embodiments 40 to 50.
75. The method according to any one of embodiments 66 to 74, wherein the conjugating is by alkyne-azide cycloaddition.
76. A method of degrading a cell surface molecule or extracellular molecule, comprising:
contacting the cell surface molecule or extracellular molecule with the bifunctional molecule of any one of embodiments 1 to 61 under conditions in which the lysosomal targeting molecule shuttles the cell surface molecule or extracellular molecule to the lysosome for degradation.

77. The method according to embodiment 76, wherein the bifunctional molecule enhances degradation of the cell surface molecule or extracellular molecule relative to degradation of the cell surface molecule or extracellular molecule in the presence of the first moiety alone.

78. The method according to embodiment 76 or embodiment 77, wherein the method is performed in vitro.

79. The method according to embodiment 76 or embodiment 77, wherein the method is performed in vivo.

80. A pharmaceutical composition comprising:
    the bifunctional molecule of any one of embodiments 1 to 61; and
    a pharmaceutically acceptable carrier.

81. The pharmaceutical composition of embodiment 80, wherein the composition is formulated for parenteral administration.

82. A method comprising administering to an individual in need thereof the pharmaceutical composition of embodiment 80 or embodiment 81.

83. A method of treating cancer comprising administering to an individual having cancer an effective amount of the pharmaceutical composition of embodiment 80 or embodiment 81.

84. The method according to embodiment 83, wherein the first moiety specifically binds to a molecule selected from the group consisting of: a cell surface molecule on a cancer cell, a ligand for a cell surface molecule on a cancer cell, a cell surface molecule on an immune cell, a ligand for a cell surface molecule on an immune cell, an inhibitory immune receptor, and a ligand of an inhibitory immune receptor.

85. The method according to embodiment 83 or embodiment 84, wherein the individual has hepatocellular carcinoma (HCC), the first moiety binds a cell surface molecule on HCC cells of the individual, and the second moiety binds ASGPR.

86. The method according to embodiment 85, wherein the first moiety binds a growth factor on HCC cells of the individual.

87. The method according to embodiment 90, wherein the first moiety binds a growth factor selected from the group consisting of: EGFR, C-Met, IGF1R, and FGFR4.

88. The method according to any one of embodiments 85 to 87, wherein the second moiety is as defined in any one of embodiments 36 to 50.

89. A method of enhancing antibody-dependent cellular cytotoxicity (ADCC) comprising administering to an individual in need al ADCC the pharmaceutical composition of embodiment 80 or embodiment 81.

90. A method of enhancing immunogenicity of a cancer in an individual, comprising administering to the individual the pharmaceutical composition of embodiment 80 or embodiment 81.

91. The method according to embodiment 89 or embodiment 90, wherein the first moiety specifically binds to a molecule selected from the group consisting of: an inhibitory Immune receptor, and a ligand of an inhibitory immune receptor.

92. The method according to any one of embodiments 82 to 91, wherein the administering is by parenteral administration.

93. The method according to any one of embodiments 82 to 91, wherein the bifunctional molecule enhances degradation of the cell surface molecule or extracellular molecule relative to degradation of the cell surface molecule or extracellular molecule in the presence of the first moiety alone.

94. A kit comprising:
    the bifunctional molecule of any one of embodiments 1 to 61; and
    instructions for degrading the cell surface molecule or extracellular molecule to which the first moiety specifically binds.

95. The kit of embodiment 94, wherein the instructions are for degrading the cell surface molecule or extracellular molecule in vitro.

96. The kit of embodiment 94, wherein the instructions are for degrading the cell surface molecule or extracellular molecule in vivo.

97. A kit comprising:
    the bifunctional molecule of any one of embodiments 1 to 61 or the pharmaceutical composition of embodiment 80 or embodiment 81; and
    instructions for administering the bifunctional molecule or pharmaceutical composition to an individual in need thereof.

98. The kit of embodiment 97, wherein the bifunctional molecule or pharmaceutical composition is present in one or more unit dosages.

99. The kit of embodiment 97, wherein the bifunctional molecule or pharmaceutical composition is present in two or more unit dosages.

100. A glycopolymer comprising:
    a polymer scaffold; and
    one or more mannose-6-phosphate receptor (M6PR) ligands attached to the polymer scaffold.

101. The glycopolymer of embodiment 100, wherein the glycopolymer is a glycoprotein comprising one or more amino acids functionalized with the one or more M6PR ligands.

102. The glycopolymer of embodiment 101, wherein the glycoprotein is a N-carboxyanhydride (NCA)-derived glycoprotein.

103. The glycopolymer of any one of embodiments 100 to 102, wherein the one or more M6PR ligands comprise one or more mannose-6-phosphates (M6P).

104. The glycopolymer of any one of embodiments 100 to 103, wherein the one or more M6PR ligands comprise one or more M6P analogs.

105. The glycopolymer of embodiment 104, wherein the one or more M6P analogs comprise one or more mannose-6-phosphonates (M6Pn).

106. The glycopolymer of any one of embodiments 100 to 105, wherein the polymer scaffold comprises from 1 to 500 M6PR ligands.

107. A method of making the glycopolymer of any one of embodiments 100 to 106, comprising:
    attaching the one or more M6PR ligands to the polymer scaffold; or
    synthesizing the polymer scaffold from monomers functionalized with the one or more M6PR ligands.

108. The method according to embodiment 107, wherein the scaffold is polymerized from one or more monomers functionalized with the one or more M6PR ligands, and wherein the synthesizing is by solid-phase synthesis.

109. The method according to embodiment 108, wherein the glycopolymer is a glycoprotein polymer, and wherein the synthesizing is by solid-phase peptide synthesis.

110. A kit comprising:
   the glycopolymer of any one of embodiments 100 to 106; and
   instructions for conjugating the glycopolymer to a molecule of interest.
111. The kit of embodiment 110, further comprising reagents for conjugating the glycopolymer to a molecule of interest.
112. The kit of embodiment 110 or embodiment 111, wherein the molecule of interest is a polypeptide.
113. The kit of embodiment 112, wherein the polypeptide is an antibody.
114. The kit of any one of embodiments 110 to 113, wherein the molecule of interest specifically binds a cell surface molecule or extracellular molecule.
115. A monomer functionalized with one or more mannose-6-phosphate receptor (M6PR) ligands.
116. The monomer of embodiment 115, wherein the monomer is an amino acid.
117. The monomer of embodiment 115, wherein the monomer is a non-natural amino acid.
118. The monomer of any one of embodiments 115 to 117, wherein the one or more M6PR ligands comprise one or more mannose-&-phosphates (M6P).
119. The monomer of any one of embodiments 115 to 118, wherein the one or more M6PR, ligands comprise one or more M6P analogs.
120. The monomer of embodiment 119, wherein the one or more M6P analogs comprise one or more mannose-6-phosphonates (M6Pn).

The following examples are offered by way of illustration and not by way of limitation.

EXPERIMENTAL

Example 1—Mannose-6-Phosphate Polymers Shuttle Cargo to Lysosomes

Figure 10:
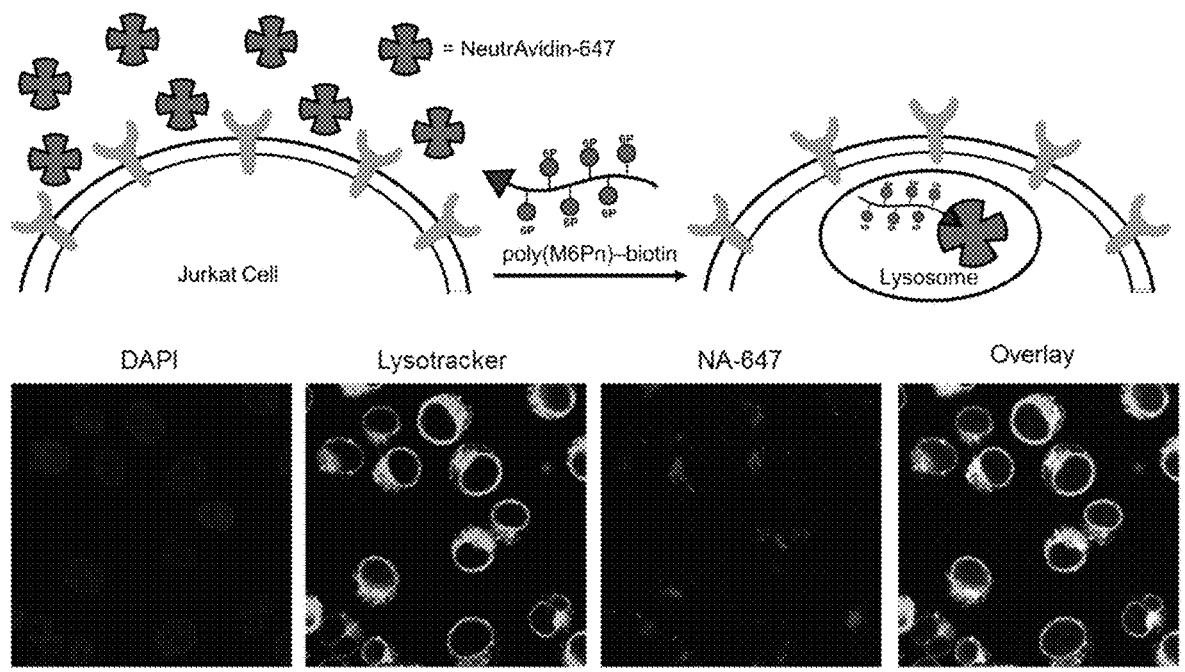
FIG. 10 A schematic illustration (top) and fluorescence imaging results (bottom) of an experiment demonstrating that M6Pn polymers which have been functionalized with a biotin cap can mediate transfer of extracellular NeutrAvidin-647 (NA647—a protein to which biotin strongly binds) to lysosomes from the extracellular space for degradation. Colocalization of both protein and lysosome staining dye are observed.

Tested in this example was a bifunctional molecule (see FIG. 10) that includes a biotin cap (the "first moiety" as used herein—depicted as a triangle in FIG. 10) and an M6Pn polymer (the "second moiety" as used herein) to determine whether the bifunctional molecule could mediate transfer of NeutrAvidin-647 (NA647—a protein to which biotin strongly binds) to lysosomes from the extracellular space for degradation. FIG. 10 provides fluorescence imaging results (bottom) demonstrating that the bifunctional molecule can indeed mediate transfer of NeutrAvidin-647 to lysosomes, as colocalization of both protein and lysosome staining dye are observed.

Figure 11:
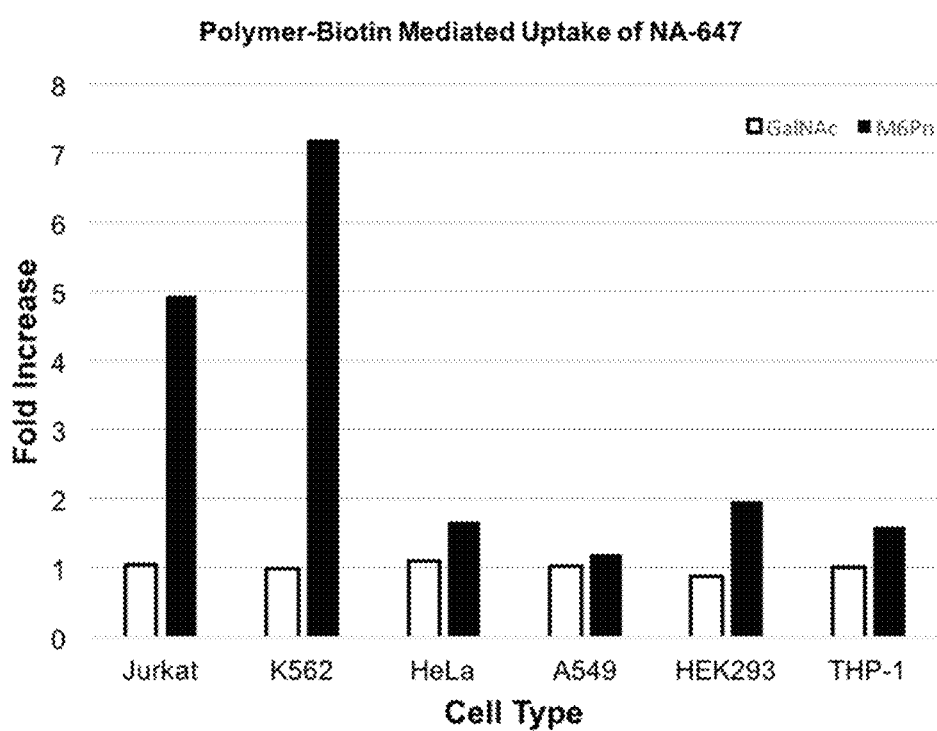
FIG. 11 Data demonstrating that several cell lines exhibit uptake of NA647 in a M6Pn polymer dependent manner. In view of these results, it is expected that any cell line bearing M6PRs (e.g., CIM6PRs) will allow for shuttling of proteins to lysosome by this method, and is not limited to the cell lines tested in the present study.

Next, various cell lines were tested in a manner as described above. Shown in FIG. 11 is data demonstrating that several cell lines exhibit uptake of NA647 in a M6Pn polymer-dependent manner. In view of these results, it is expected that any cell line bearing M6PRs (e.g., CIM6PRs) will allow for shuttling of cell surface and extracellular molecules to the lysosome by this method, and is not limited to the cell lines tested in the present study.

Example 2—M6Pn-Conjugated Antibodies Shuttle Targets to Lysosomes

Tested in this example were bifunctional molecules in which the first moiety is an antibody that binds to a particular target of interest and the second moiety is a M6Pn-containing glycoprotein.

Figure 13:
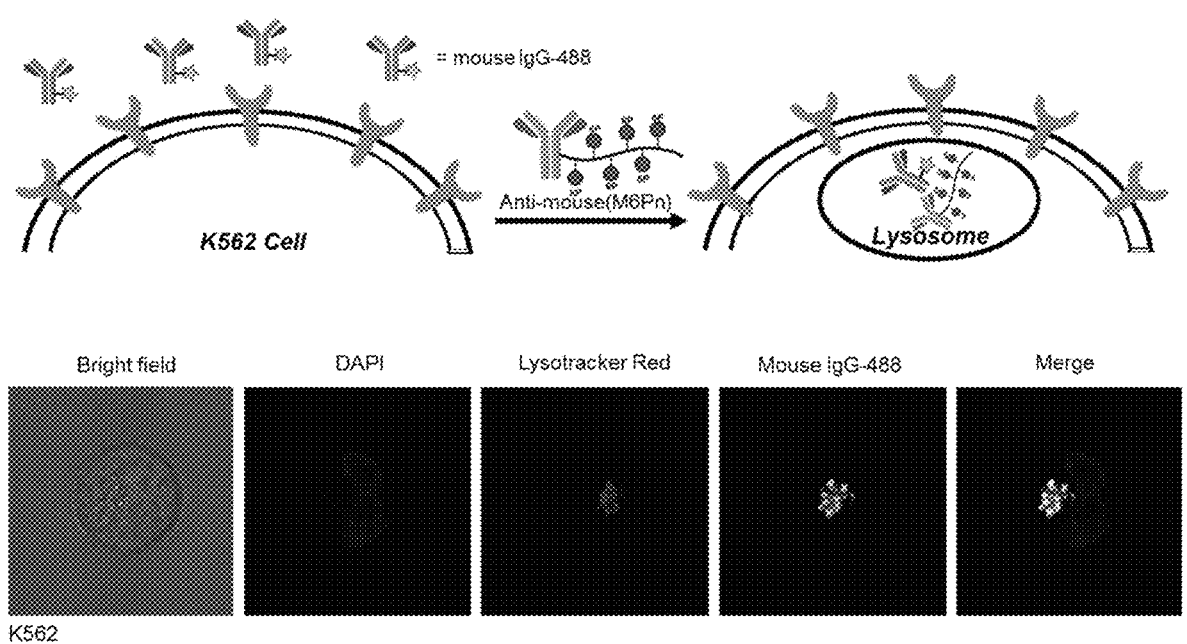
FIG. 13 Schematic illustration (top) and fluorescence imaging data (bottom) demonstrating that poly(M6Pn) labeled antibodies can shuttle their binding partners to lysosomes. In this example, a mouse IgG-488 was incubated with an anti-mouse IgG antibody bearing the poly(M6Pn) tag, with colocalization of both protein and lysosome staining dye (merge).

Provided in FIG. 13 is a schematic illustration (top) and fluorescence imaging data (bottom) demonstrating that poly (M6Pn) labeled antibodies can shuttle their binding partners to lysosomes. In this example, a rouse IgG-488 was incubated with an anti-mouse IgG antibody bearing the poly (M6Pn) tag, with colocalization of both protein and lysosome staining dye (merge).

Figure 14:
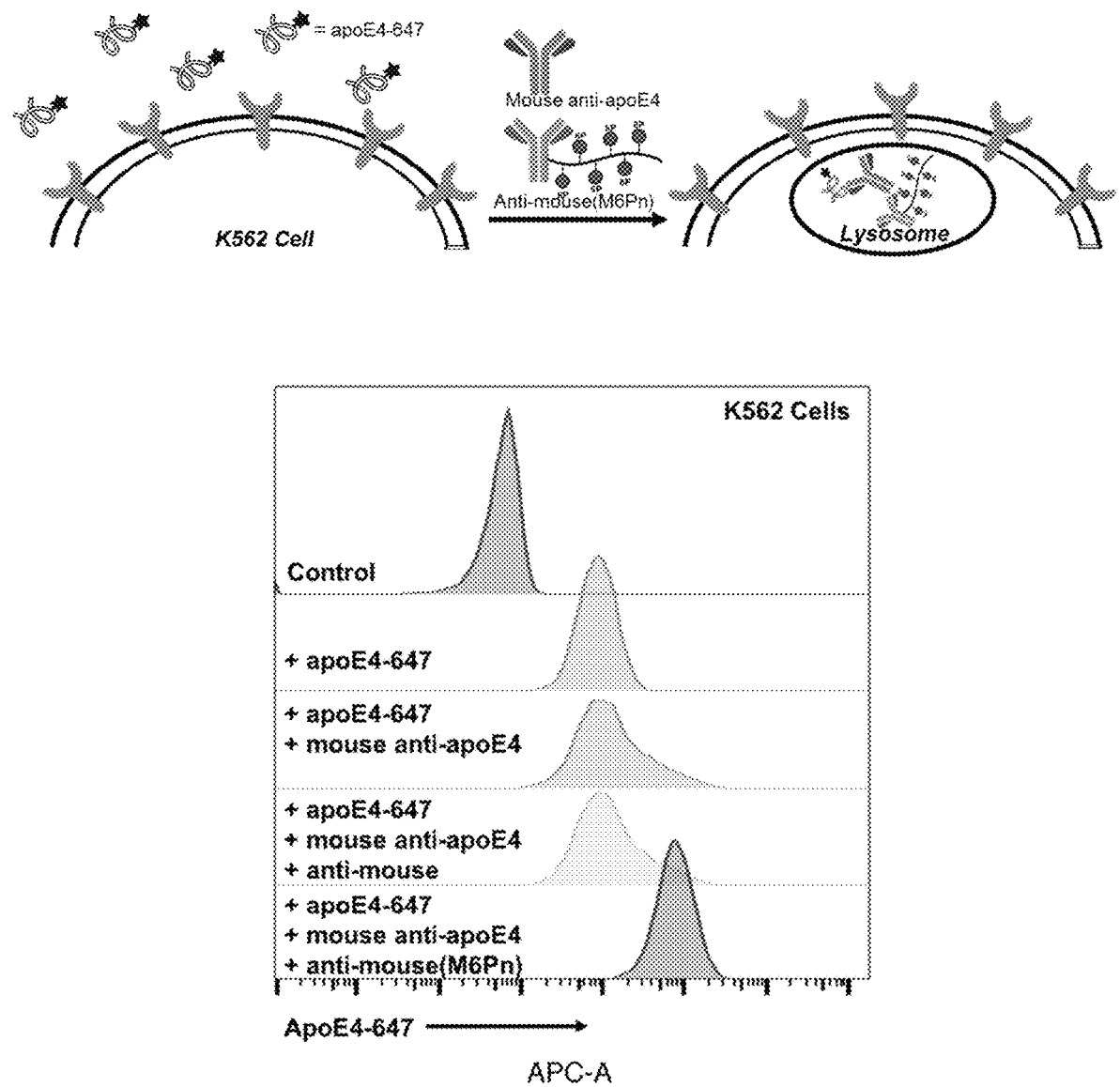
FIG. 14 Schematic illustration (top) and data (bottom) demonstrating that poly(M6Pn) labeled antibodies can shuttle their binding partners to intracellular compartments. In this example, recombinant human apoE4 was incubated with a mouse-derived anti-human apoE4 antibody, an anti-mouse IgG antibody, or an anti-mouse antibody bearing the poly(M6Pn) tag. Significantly more uptake is observed with the M6Pn-containing secondary antibody.

Provided in FIG. 14 is a schematic illustration (top) and further data (bottom) demonstrating that poly(M6Pn) labeled antibodies can shuttle their binding partners to intracellular compartments. In this example, recombinant human apoE4 was incubated with a mouse-derived anti-human apoE4 antibody, an anti-mouse IgG antibody, or an anti-mouse antibody bearing the poly(M6Pn) tag. Significantly more uptake is observed with the M6Pn-containing secondary antibody.

Figure 15:
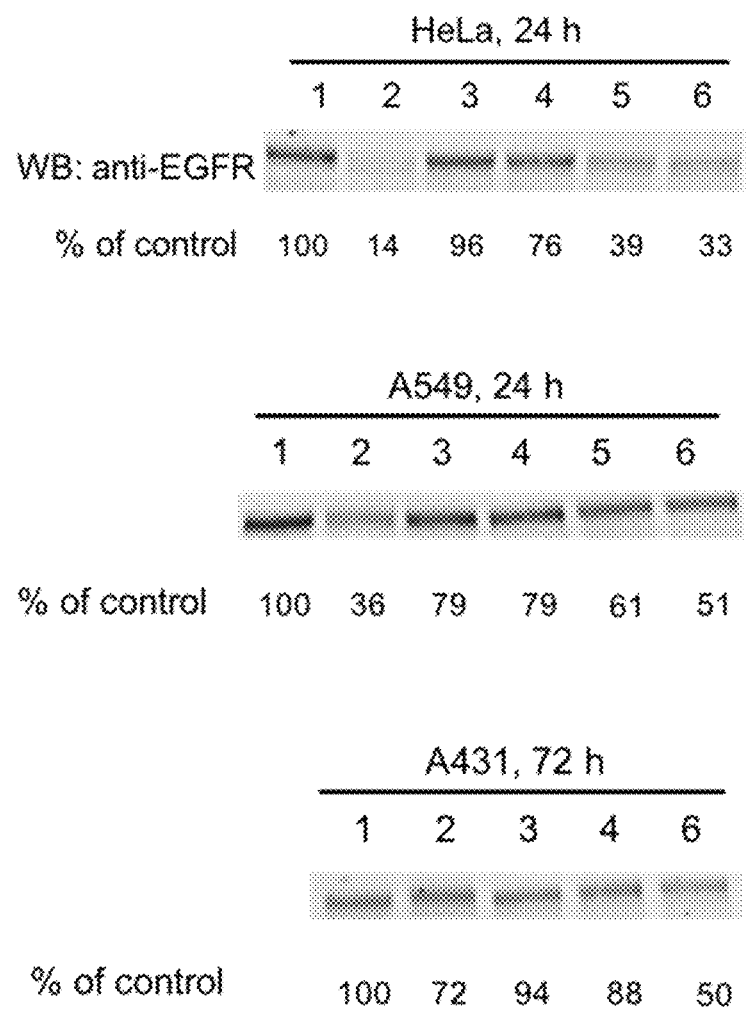
FIG. 15 Data demonstrating that poly(M6Pn) labeled antibodies can shuttle their binding partners for degradation. In this example, EGFR degradation was assessed by incubating cells with cetuximab bearing an M6Pn tag. Loss of total EGFR is observed for all cell lines tested, compared to cetuximab or cetuximab bearing a mock polymer (GalNAc). EGF is a positive control for EGFR degradation. Lane 1: control. Lane 2: EGF (100 ng/mL, 1 h, + control). Lane 3: cetuximab. Lane 4: cetuximab-GalNAc conjugate. Lane 5: cetuximab-M6P conjugate (long). Lane 6: cetuximab-M6P conjugate (short). Percent of control was calculated by densitometry.

Provided in FIG. 15 is further data demonstrating that poly(M6Pn) labeled antibodies can shuttle their binding partners for degradation. In this example, EGFR degradation was assessed by incubating cells with cetuximab bearing an M6Pn tag. Loss of total EGFR is observed for all cell lines tested, compared to cetuximab or cetuximab bearing a mock polymer (GalNAc). EGF is a positive control for EGFR degradation. Lane 1: control. Lane 2: EGF (100 ng/mL, 1 h, + control). Lane 3: cetuximab. Lane 4: cetuximab-GalNAc conjugate. Lane 5: cetuximab-M6P conjugate (long). Lane 6: cetuximab-M6P conjugate (short). Percent of control was calculated by densitometry.

Figure 16:
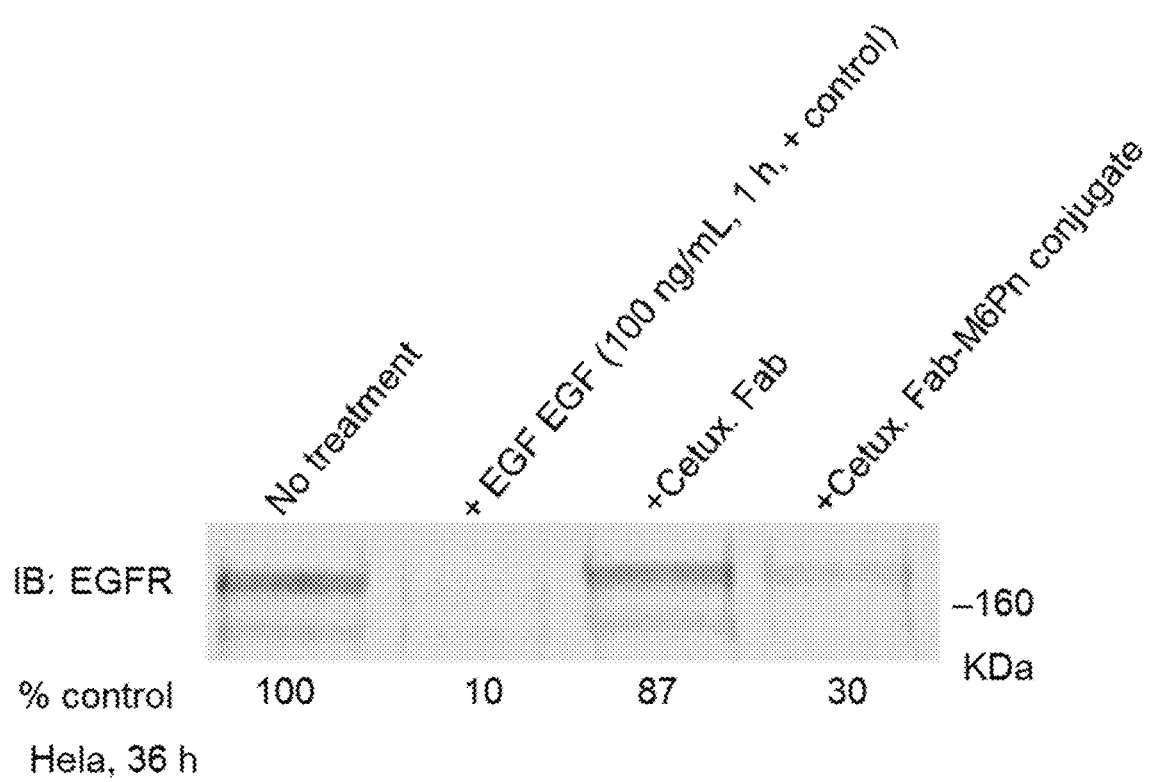
FIG. 16 Data demonstrating that poly(M6Pn) labeled antibody fragments can shuttle their binding partners to lysosomes. In this example, EGFR degradation was assessed by incubating cells with cetuximab-derived Fab portions bearing an M6Pn tag. Loss of total EGFR is observed compared to cetuximab Fab alone or cetuximab Fab bearing a mock polymer (GalNAc).

Provided in FIG. 16 is data demonstrating that poly (M6Pn) labeled antibody fragments can shuttle their binding partners for degradation. In this example, EGFR degradation was assessed by incubating cells with cetuximab-derived Fab portions bearing an M6Pn tag. Loss of total EGFR is observed compared to cetuximab Fab alone or cetuximab Fab bearing a mock polymer (GalNAc).

Figure 17:
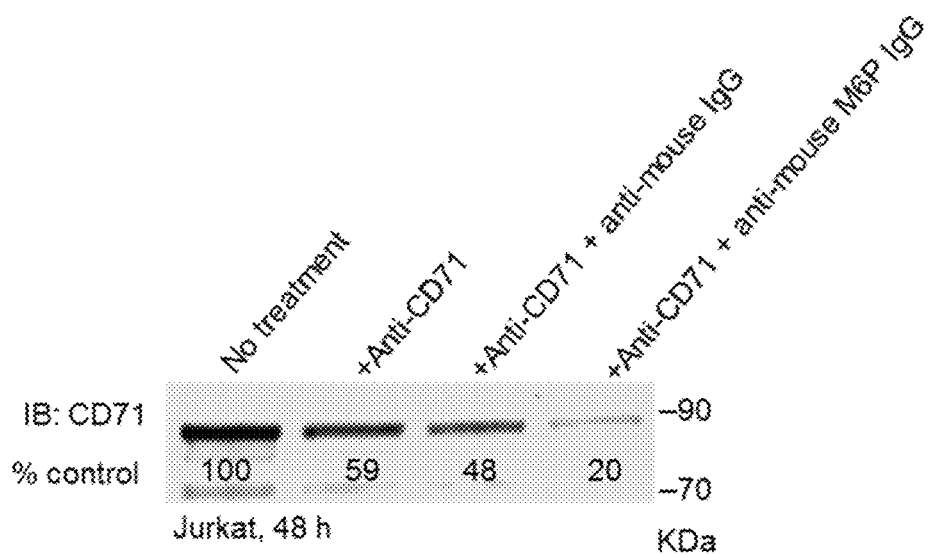
FIG. 17 Data demonstrating that poly(M6Pn) labeled antibodies can shuttle their binding partners for degradation. In this example, degradation of CD71 (transferrin receptor) was assessed by incubating cells with a primary mouse-derived antibody against CD71, an anti-mouse IgG antibody, or an anti-mouse antibody bearing the poly(M6Pn) tag. The system containing the M6P tag leads to significantly more degradation.

Provided in FIG. 17 is further data demonstrating that poly(M6Pn) labeled antibodies can shuttle their binding partners for degradation. In this example, degradation of CD71 (transferrin receptor) was assessed by incubating cells with a primary mouse-derived antibody against CD71, an anti-mouse IgG antibody, or an anti-mouse antibody bearing the poly(M6Pn) tag. The system containing the M6P tag leads to significantly more degradation.

Figure 18:
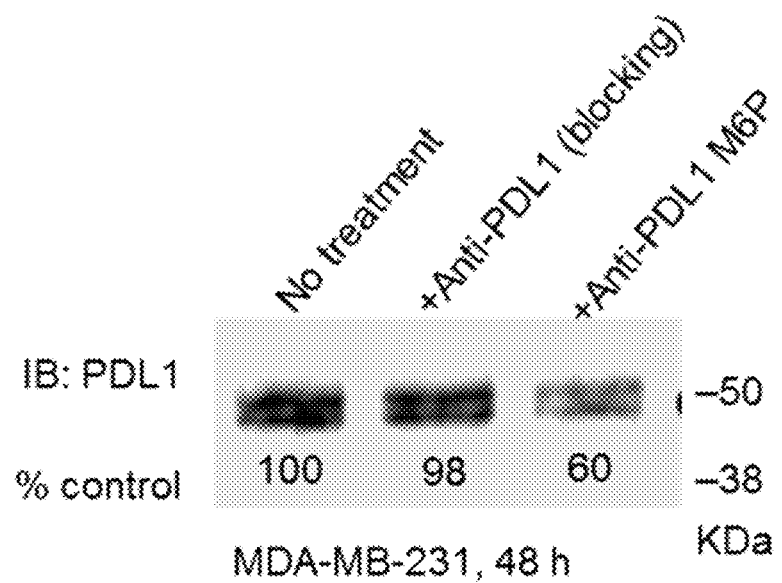
FIG. 18 Data demonstrating that poly(M6Pn) labeled antibodies fragments can shuttle their binding partners for degradation. In this example, PDL1 degradation was assessed by incubating cells with anti-PDL1 antibody or anti-PDL1 antibody bearing an M6P tag. Degradation is only observed with M6P-labeled anti-PDL1 antibody.

Provided in FIG. 18 is further data demonstrating that poly(M6Pn) labeled antibodies can shuttle their binding partners for degradation. In this example, PDL1 degradation was assessed by incubating cells with anti-PDL1 antibody or anti-PDL1 antibody bearing an M6P tag. Degradation is only observed with M6P-labeled anti-PDL1 antibody.

Example 3—ASGPR Ligands Shuttle Cargo to Lysosomes in Hepatocytes

Figure 20:
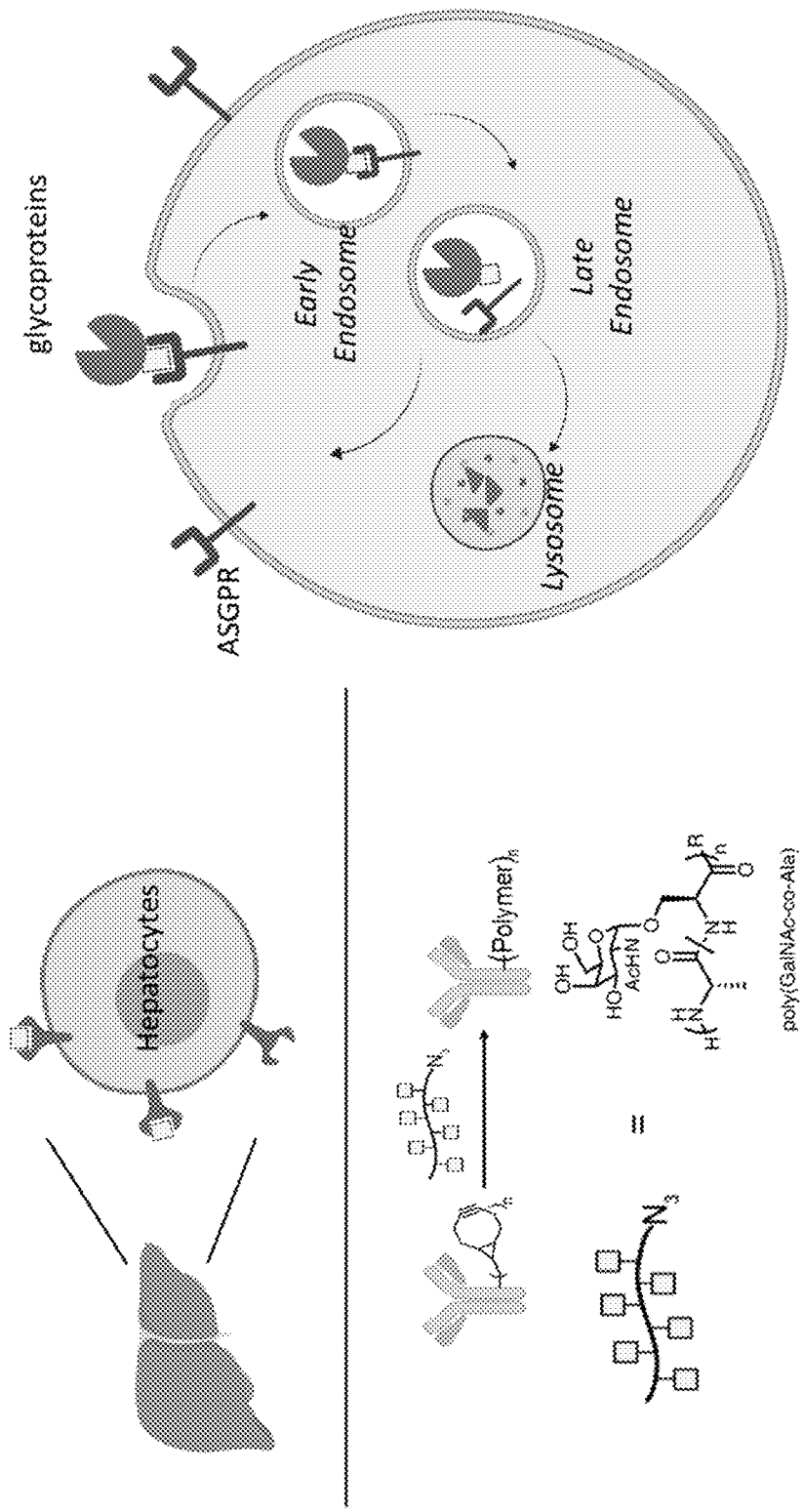
FIG. 20 Schematic illustration of a lysosomal targeting molecule to which the second moiety of a bifunctional molecule may bind according to embodiments of the present disclosure. In this example, the lysosomal targeting molecule is asialoglycoprotein receptor (ASGPR) which is expressed substantially exclusively on liver cells, e.g., hepatocytes. As shown on the right, ASGPR constitutively recycles between the plasma membrane and the endosome, thereby bringing extracellular glycoproteins inside the cell for degradation in the lysosome. Shown on the lower left is an example bifunctional molecule comprising a first moiety that is an antibody (e.g., an antibody that binds a molecule expressed on the surface of hepatocytes or a molecule present in the extracellular space of hepatocytes) and a second moiety comprising multivalent ASGPR ligands for binding to ASGPR. In this example, the second moiety comprises a polymer of N-acetylgalactosamines (GalNAc), in particular a poly(GalNAc-co-Ala) polymer as shown.

Several current therapies suffer from off target effects. Described in this example is the targeted degradation of proteins in the liver which may be employed to treat liver-related diseases such as liver cancer and liver fibrosis. A scavenger receptor called asialoglycoprotein receptor (ASGPR) is exclusively or near-exclusively expressed in liver cells (hepatocytes). As schematically illustrated in FIG. 20 (left), ASGPR constitutively recycles between the plasma membrane and the endosome. ASGPR brings extracellular glycoproteins inside the cell for degradation in the lysosome. Demonstrated herein is the harnessing of this receptor for degrading extracellular or membrane proteins on hepatocytes using a bifunctional molecule comprising a first moiety that binds to such a membrane or extracellular protein and a second moiety comprising ASGPR ligands.

Tested in the ASGPR-related examples herein were bifunctional molecules that comprise an antibody that binds to a target molecule to be degraded conjugated to a second moiety comprising a polymer of N-acetylgalactosamines (GalNAc), in particular a poly(GalNAc-co-Ala) polymer as shown in FIG. 20 (lower left).

Figure 21:
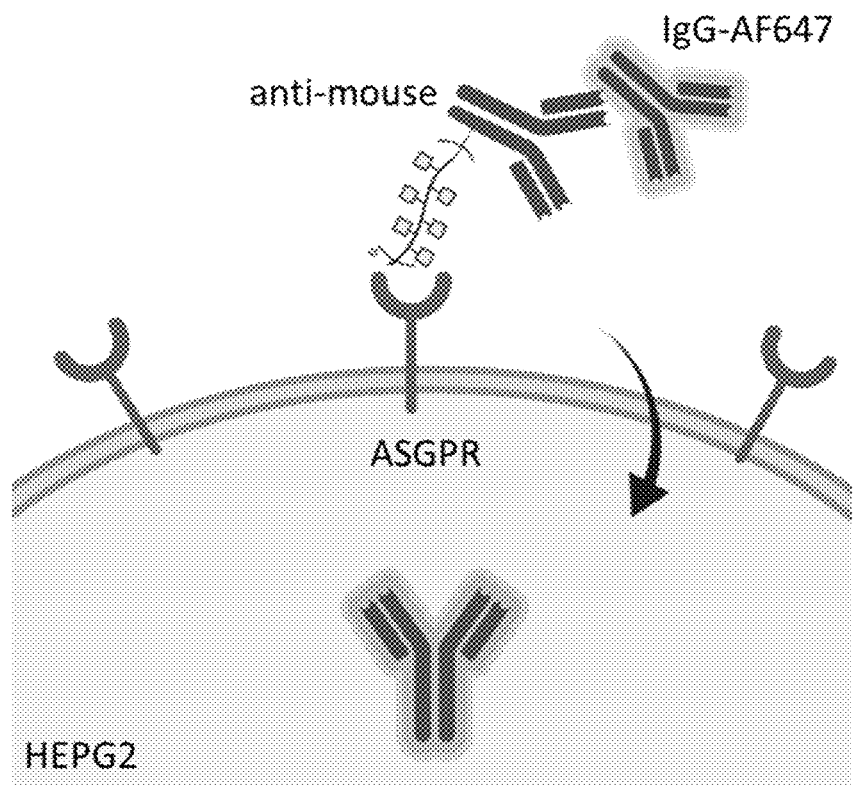
FIG. 21 Schematic illustration and data demonstrating import of target molecules into HEFG2 (hepatocellular carcinoma) cells using a bifunctional molecule comprising a first moiety (in this example, an antibody) that binds to the target molecule and a second moiety comprising the GalNAc-containing polymer shown in FIG. 20.
Figure 21:
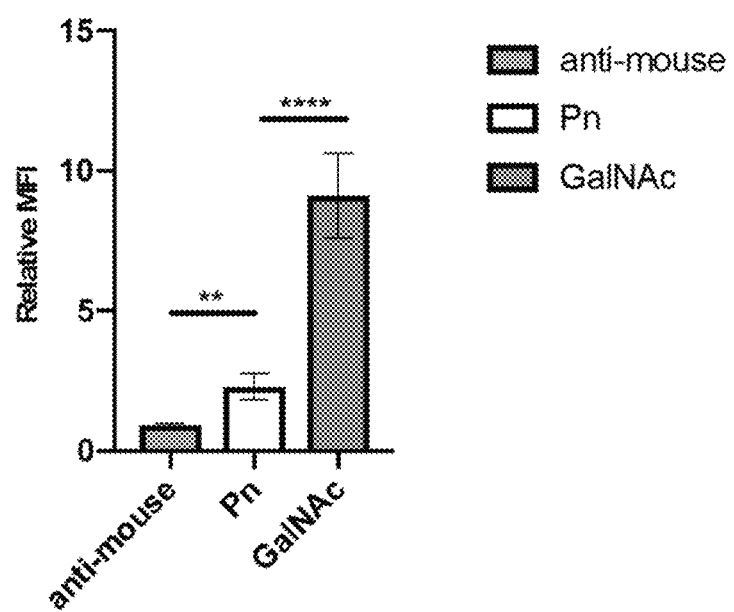

To assess whether a bifunctional molecule comprising ASGPR ligands could indeed shuttle cargo to lysosomes in hepatocytes, an assay schematically illustrated in FIG. 21 was employed. A bifunctional molecule comprising an anti-mouse IgG antibody conjugated to a poly(GalNAc-co-Ala) polymer was tested to determine whether the bifunctional molecule could shuttle extracellular fluorescent-labeled mouse IgG (IgG-AF647) into the intracellular compartment of hepatocytes. Also tested in this example was a bifunctional molecule comprising the anti-mouse IgG antibody conjugated to M6PR ligands. HEPG2 cells (hepatocellular carcinoma cell line) were incubated with 50 nM IgG-AF647 and 25 nM of anti-mouse conjugates for 1 hour. Cellular uptake was analyzed by flow cytometry. As shown by the bar graph, an approximately 8-fold increase in cell fluorescence was observed using the GalNAc-containing conjugate while the M6Pn-containing conjugate induced 2-fold increase over background. The data demonstrate that in hepatocytes, where the expression level of ASGPR is higher than that of M6PR, the GalNAc-containing conjugate is more effective in triggering cellular uptake.

Figure 22:
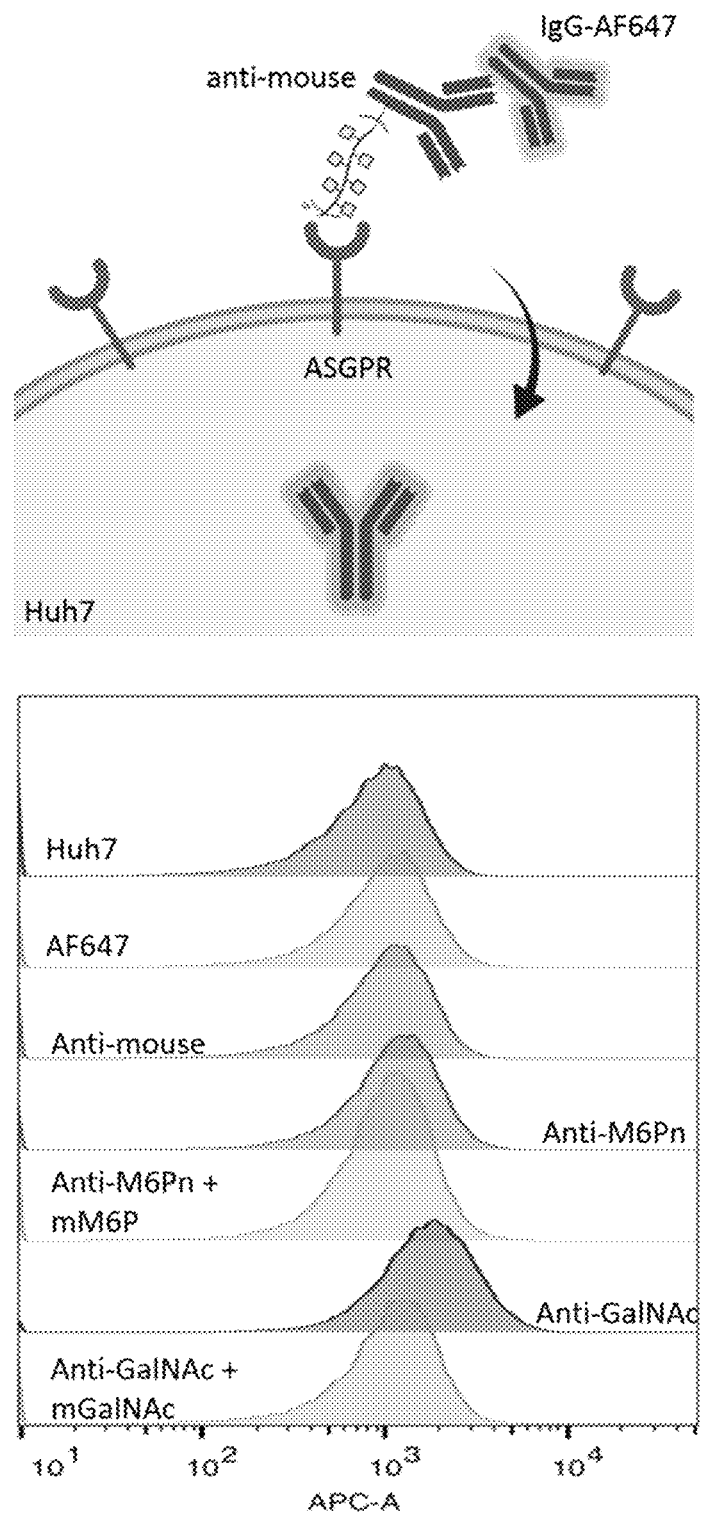
FIG. 22 Schematic illustration and data demonstrating efficient cellular uptake via ASGPR in HUH7 (hepatocellular carcinoma) cells.

Shown in FIG. 22 are results from the assay described for FIG. 21 but in HUH7 cells (another hepatocellular carcinoma cell line). Efficient uptake of IgG-AF647 into the HUH7 cells was observed. In addition, controls were included in which the cells were incubated with M6PR or ASGPR inhibitors (monomeric M6P (mM6P) and monomeric GalNAc (mGalNAc), respectively). Uptake was reduced when the cells were incubated with the inhibitors, indicating that the uptake with GalNAc- or M6Pn-containing conjugates is indeed mediated by ASGPR or M6PR, respectively.

Example 4—Efficient Degradation of EGFR in Hepatocytes Using Cetuximab-ASGPR Ligand Conjugates Epidermal growth factor receptor (EGFR) is known to induce proliferation and angiogenesis in hepatocellular carcinoma (HCC). 68% of HCC patients express EGFR on their HCC cells. Transplantation currently remains the best treatment option for patients with HCC, and the supply of good-quality deceased donor organs is limited. Receptor-tyrosine kinase (RTK) inhibitors or antibodies are often used for treatment, but HCC cells develop resistance to these treatments due to the heterodimerization of the receptor tyrosine kinases (EGFR, HER2, HER3, c-Met, IGF1R) which leads to the phosphorylation of the same downstream effectors to restore oncogenic signaling via RTK crosstalk. Cetuximab, an EGFR blocking antibody, failed in Phase II Clinical Trials in HCC patients.

Figure 23:
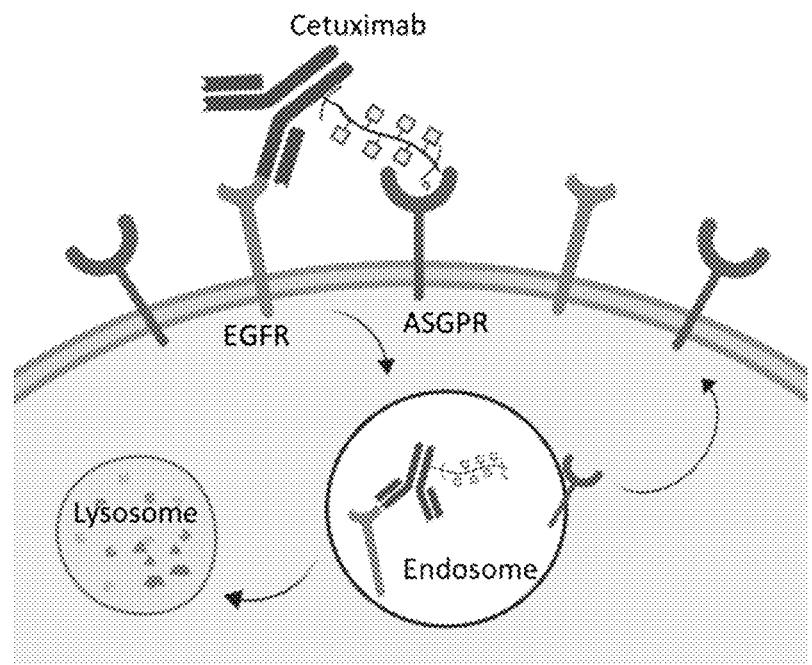
FIG. 23 Schematic illustration and data demonstrating efficient degradation of EGFR in HEP3B (hepatocellular carcinoma) cells using a bifunctional molecule comprising Cetuximab (first moiety) conjugated to a second moiety comprising the GalNAc-containing polymer shown in FIG. 20. Also shown is EGFR degradation data for a conjugate comprising Cetuximab (first moiety) conjugated to a second moiety comprising M6PR ligands.
Figure 23:
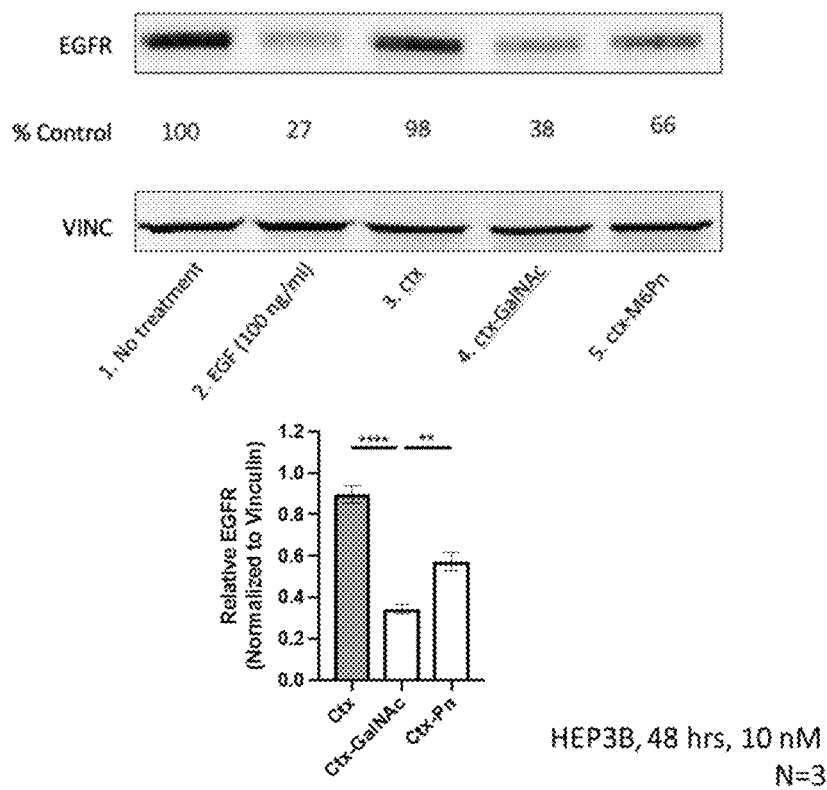

Assessed in this example was whether a bifunctional molecule comprising an anti-EGFR antibody (Cetuximab in this example) conjugated to ASGPR ligands (poly(GalNAc-co-Ala) in this example) could induce uptake and degradation of EGFR in HCC cells, as schematically illustrated in FIG. 23 (top). Also tested were Cetuximab-M6PR ligand conjugates.

HEP3B cells were used in a first experiment. The cells were incubated with 10 nM of cetuximab conjugates for 48 hours and then lysed for western blot analysis. The western blot (shown in FIG. 23, bottom) has 5 lanes: 1) no treatment, 2) EGF (known down-regulator of EGFR), 3) cetuximab, 4) cetuximab-GalNAc, conjugate, and 5) cetuximab-M6Pn conjugate. As shown, the Cetuximab-GalNAc conjugate exhibited efficient EGRFR degradation and greater EGFR degradation as compared to the Cetuximab-M6Pn conjugate. Vinculin was used as a loading control.

Figure 24:
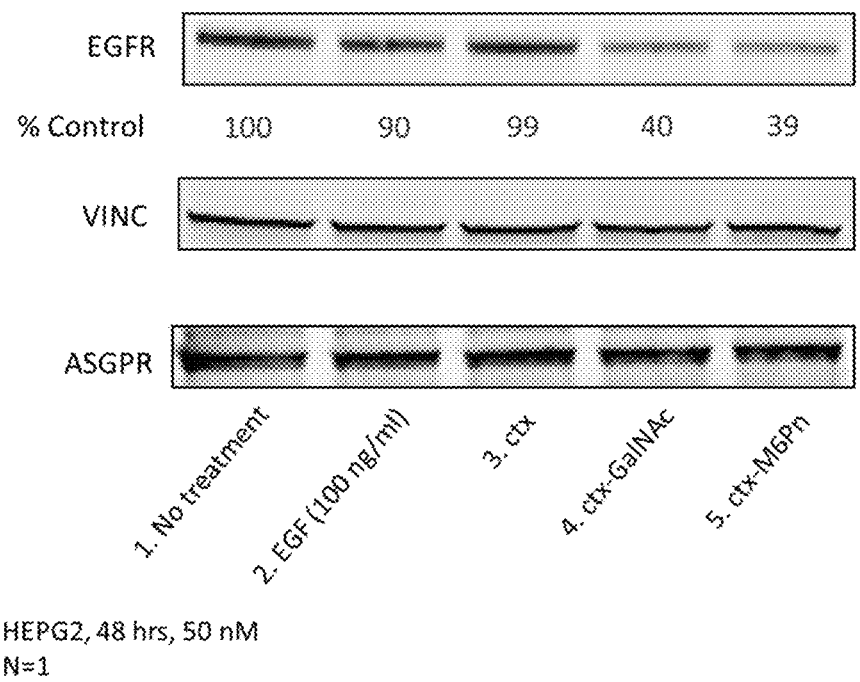
FIG. 24 Data demonstrating efficient degradation of EGFR in HEPG2 cells using a bifunctional molecule comprising Cetuximab (first moiety) conjugated to a second moiety comprising the GalNAc-containing polymer shown in FIG. 20. Also shown is EGFR degradation data for a conjugate comprising Cetuximab (first moiety) conjugated to a second moiety comprising M6PR ligands.
Figure 24:
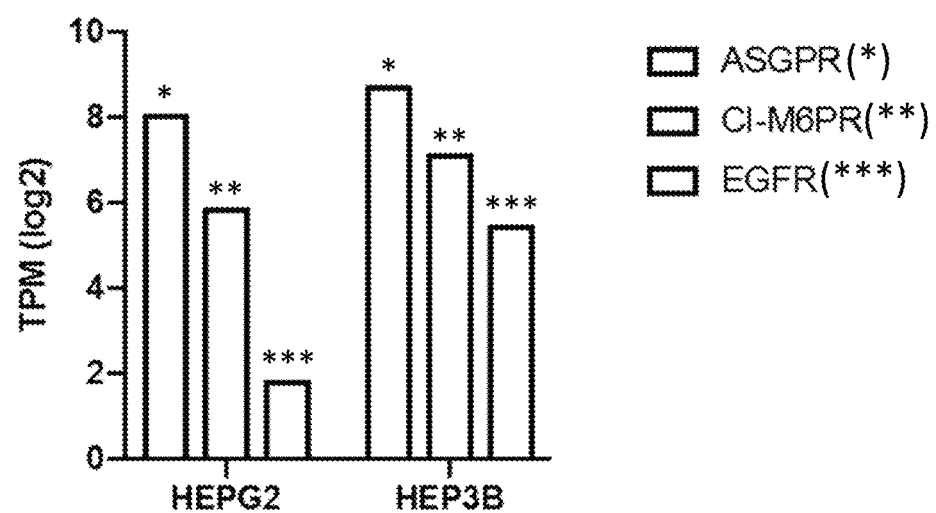

HEPG2 cells were used in a second experiment. Results are shown in FIG. 24. Efficient degradation of EGFR in HEPG2 cells was observed. Here, the degradation efficiency was similar between the cetuximab-GalNAc and cetuximab-M6Pn conjugates, possibly due to the relative levels of EGFR in the HEP3B and HEPG2 cell lines. Shown on the right are relative mRNA levels of the receptors and EGFR in the two cell lines (available in public database). Since EGER levels are relatively low in HEFG2 cells compared to HEP3B cells, the data suggest that even with a less effective degrader (cetuximab-M8Pn conjugate), most of the membrane EGFR is being degraded, and that residual EGFR seen in the western blot may be internal EGFR. ASGPR levels were also monitored to show that the level of ASGPR remained constant throughout the different treatments.

Figure 25:
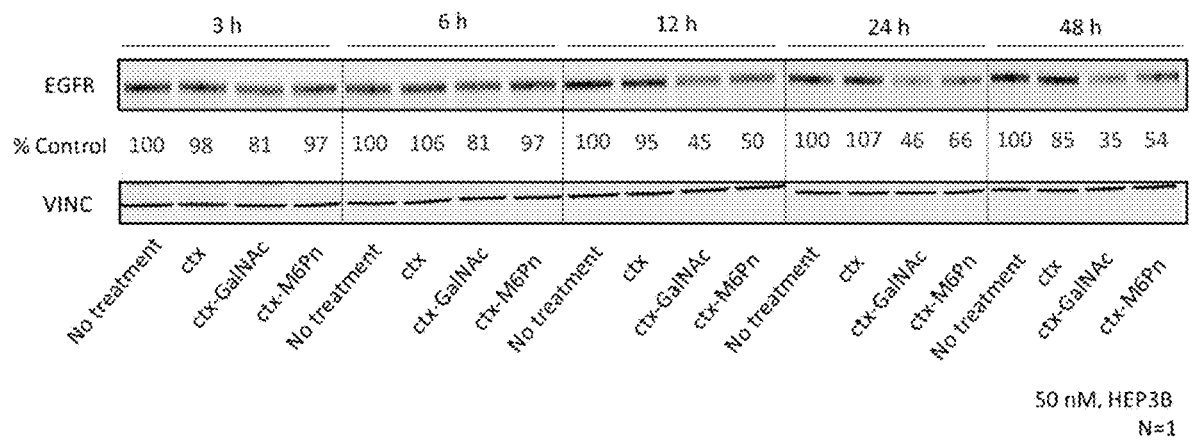
FIG. 25 Data from a time-course study assessing EGFR degradation over time in HEP3B cells.

Next, a time-course study was performed to assess EGFR degradation over time in HEP3B cells treated with the cetuximab conjugates. Results are shown in FIG. 25. As shown, by 12 hours, the cetuximab-GalNAc conjugates reduces EGFR levels below 50%. The degradation increases at 48 hours. The cetuximab-M6Pn conjugate did not reduce EGFR levels below 50% at any of the time points tested.

Figure 26:
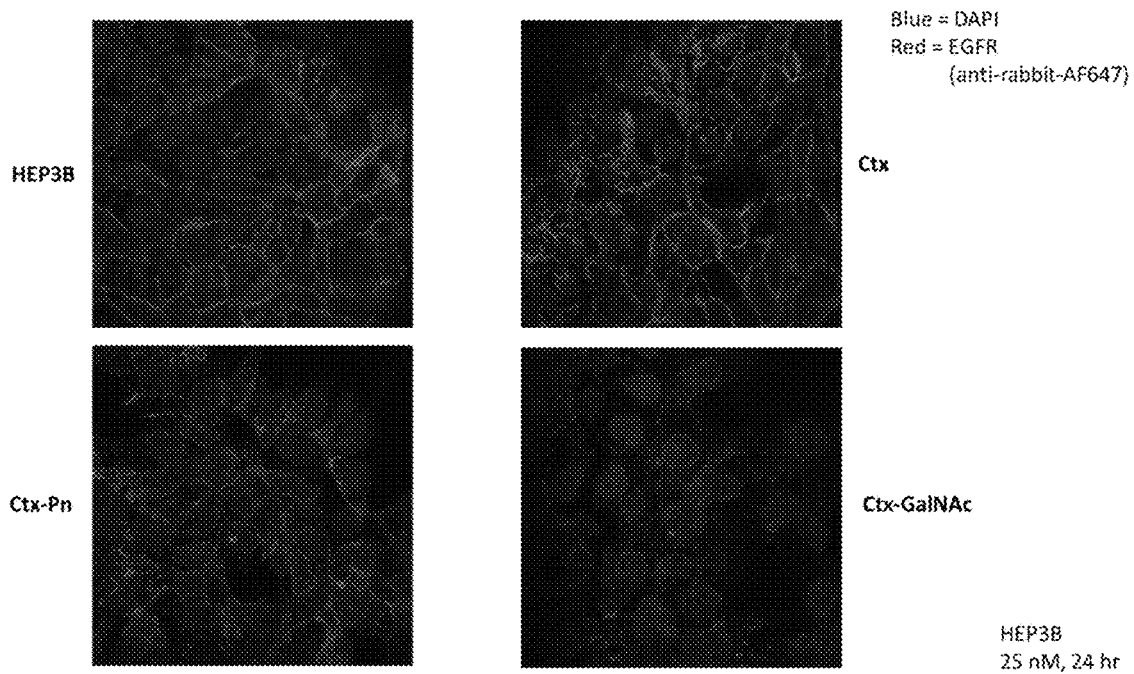
FIG. 26 Immunofluorescence data demonstrating that treatment of HEP3B cells using the Cetuximab conjugates described above degrades the majority of membrane EGFR, whereas residual EGFR is internal to the cells.

Immunofluorescence experiments were performed to assess whether the residual EGFR is membrane EGFR or intracellular EGFR. Results are shown in FIG. 26. The outlines of the cells in HEF3B and cetuximab indicate EGFR localization on the membrane. When HEP3B was treated with cetuximab-M6Pn conjugate, some of the EGFR is localized internally while some remains on the membrane. When HEP3B is treated with cetuximab-GalNAc conjugate, almost no EGFR is observed on the membrane, and the vast majority of the EGFR is inside the cells. Accordingly, the cetuximab-GalNAc conjugate degraded most membrane-bound EGFR, and the residual (approx. 30%) EGFR seen on the western blot appears to be intracellular EGFR.

Example 5—HER2 Degradation Via Trastuzumab Alone and Trastuzumab Conjugates

Figure 27:
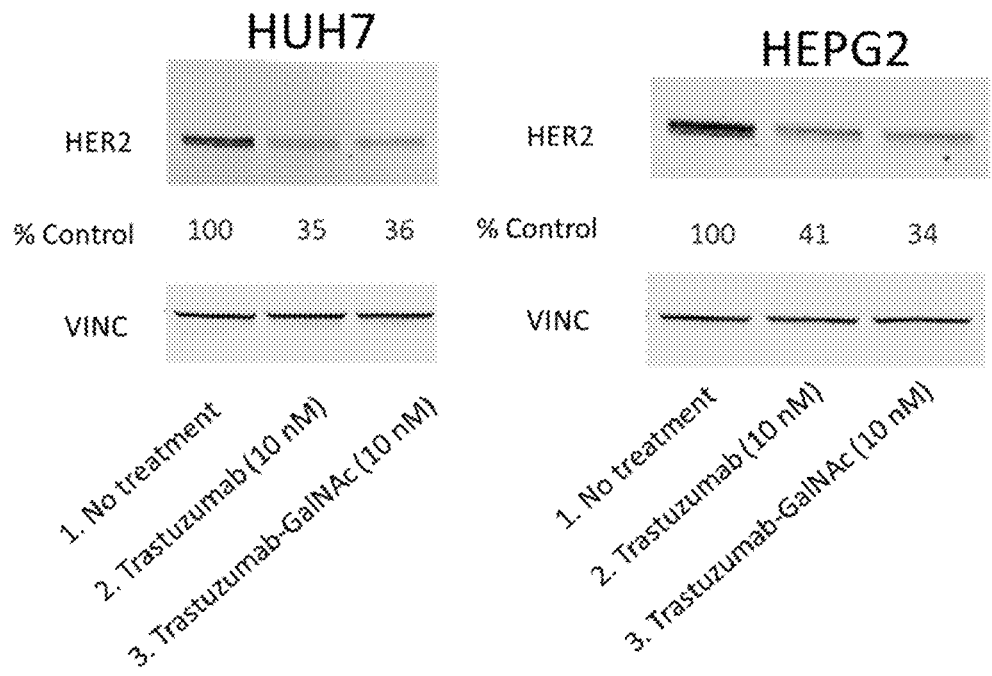
FIG. 27 Western blot data showing the extent of degradation of HER2 in HUH7 and HEPG2 cells in the presence of Trastuzumab alone or Trastuzumab conjugated to a GalNAc-containing polymer.
Figure 27:
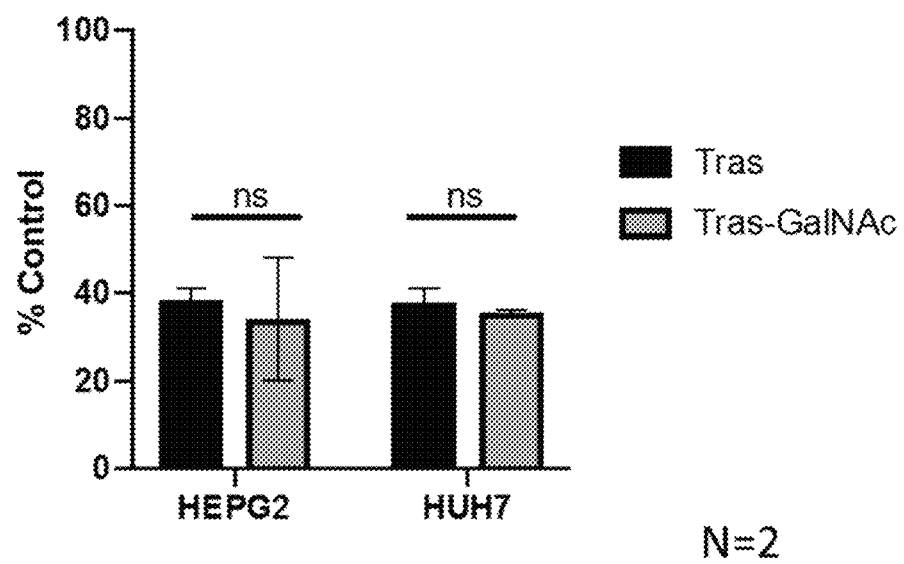

Assessed in this example was the extent of degradation of HER2 in HUH7 and HEPG2 cells in the presence of Trastuzumab alone or Trastuzumab conjugated to the Gal-NAc-containing polymer shown in FIG. 20 ("Trastuzumab-GalNAc"). HUH7 and HEPG2 cells were incubated with 10 nM of trastuzumab or trastuzumab-GalNAc conjugates for 48 hours and then lysed for western blot analysis. The western blot in FIG. 27 has 3 lanes for each cell line: 1) no treatment, 2) trastuzumab, 3) trastuzumab-GalNAc. The bar graph in FIG. 27 shows average percent of HER2 relative to the control in each cell line. As shown, there was no statistical difference in HER2 degradation in the presence of trastuzumab alone or trastuzumab conjugated to the GalNAc-containing polymer in either cell line. As such, the Trastuzumab-GalNAc conjugate did not enhance degradation of HER2 relative to degradation of HER2 in the presence of Trastuzumab alone.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein.

What is claimed is:

1. A bifunctional molecule comprising:
    a first moiety that specifically binds a cell surface molecule or extracellular molecule, wherein the first moiety is selected from an antibody, an antigen, a ligand, and a small molecule; and
    a second moiety comprising a polymer scaffold that displays one or more mannose-6-phosphate (M6P) analogs that specifically binds a mannose-6-phosphate receptor (M6PR),
    wherein the first moiety and the second moiety are covalently attached via a linker.

2. The bifunctional molecule of claim 1, wherein the first moiety specifically binds a cell surface molecule.

3. The bifunctional molecule of claim 2, wherein the cell surface molecule is a cell surface receptor.

4. The bifunctional molecule of claim 1, wherein the first moiety specifically binds an extracellular molecule.

5. The bifunctional molecule of claim 4, wherein the extracellular molecule is a ligand for a cell surface receptor.

6. The bifunctional molecule of claim 5, wherein the extracellular molecule is a growth factor, a cytokine, or a chemokine.

7. The bifunctional molecule of claim 4, wherein the extracellular molecule is an autoantibody and the first moiety is an antigen for the autoantibody.

8. The bifunctional molecule of claim 4, wherein the extracellular molecule is selected from a secreted protein that accumulates in disease, a cholesterol carrier, an infectious disease toxin, an infectious particle, a clotting factor, a chemokine or cytokine, a proteinaceous hormone, a proteinaceous mediator of a mood disorder, a proteinaceous mediator of energy homeostasis, a proteinaceous allergen present in the bloodstream or an antibody against such an allergen, and a proteinaceous toxin.

9. The bifunctional molecule of claim 4, wherein the extracellular molecule is an antibody.

10. The bifunctional molecule of claim 1, wherein the first moiety is a small molecule.

11. The bifunctional molecule of claim 1, wherein the first moiety is a protein antigen or protein ligand.

12. The bifunctional molecule of claim 11, wherein the one or more M6P analogs comprise one or more mannose-6-phosphonates (M6Pn).

13. The bifunctional molecule of claim 11, wherein the second moiety is a glycoprotein comprising one or more amino acids functionalized with the M6P analogs.

14. The bifunctional molecule of claim 1, wherein the first moiety is an antibody.

15. The bifunctional molecule of claim 14, wherein the antibody is an IgG, single chain Fv (scFv), Fab, (Fab)$_2$, (scFv')$_2$, or nanobody.

16. The bifunctional molecule of claim 1, wherein the one or more M6P analogs comprise one or more mannose-6-phosphonates (M6Pn).

17. The bifunctional molecule of claim 16, wherein the second moiety is a glycoprotein comprising one or more amino acids functionalized with the one or more M6Pn.

18. A bifunctional protein conjugate comprising:
    a first moiety comprising a protein that specifically binds a cell surface molecule or an extracellular molecule; and
    a second moiety comprising a polymer scaffold that displays one or more mannose-6-phosphate (M6P) analogs that specifically bind a mannose-6-phosphate receptor (M6PR),
    wherein the first moiety and the second moiety are conjugated via a linker.

19. The bifunctional protein conjugate of claim 18, wherein the first moiety specifically binds the extracellular molecule.

20. The bifunctional protein conjugate of claim 19, wherein the extracellular molecule is an antibody, and the first moiety comprises a protein antigen of the antibody.

21. The bifunctional protein conjugate of claim 20, wherein the extracellular molecule is an autoantibody.

22. The bifunctional protein conjugate of claim 18, wherein the first moiety specifically binds the cell surface molecule.

23. The bifunctional protein conjugate of claim 18, wherein the first moiety is an antibody, a protein antigen, or a protein ligand.

24. The bifunctional protein conjugate of claim 18 wherein each of the one or more M6P analogs comprise a 6-phosphonate group.

25. The bifunctional protein conjugate of claim 24, wherein the second moiety is a glycoprotein comprising one or more amino acids functionalized with one or more mannose-6-phosphonates (M6Pn).

26. The bifunctional protein conjugate of claim 25, wherein the one or more M6P analogs comprise one or more mannose-6-phosphonates (M6Pn).

27. The bifunctional protein conjugate of claim 18, wherein the first moiety is an antibody.

28. The bifunctional protein conjugate of claim 27, wherein each of the M6P analogs comprise a phosphonate group.

29. The bifunctional protein conjugate of claim 28, wherein the second moiety is a glycoprotein comprising one or more amino acids functionalized with one or more mannose-6-phosphonates (M6Pn).

30. The bifunctional protein conjugate of claim 18, wherein the first moiety is a protein ligand.

31. The bifunctional protein conjugate of claim 30, wherein each of the M6P analogs comprise a 6-phosphonate group.

32. The bifunctional protein conjugate of claim 31, wherein the second moiety is a glycoprotein comprising one or more amino acids functionalized with one or more mannose-6-phosphonates (M6Pn).

33. The bifunctional protein conjugate of claim 18, wherein the first moiety is a protein antigen.

34. The bifunctional protein conjugate of claim 33, wherein each of the M6P analogs comprise a 6-phosphonate group.

35. The bifunctional protein conjugate of claim 34, wherein the second moiety is a glycoprotein comprising one or more amino acids functionalized with one or more mannose-6-phosphonates (M6Pn).

* * * * *